(12) United States Patent
Hanna et al.

(10) Patent No.: US 8,263,339 B2
(45) Date of Patent: Sep. 11, 2012

(54) ABSCRIPTION BASED MOLECULAR DETECTION

(75) Inventors: Michelle M. Hanna, Carlsbad, CA (US); David McCarthy, Carlsbad, CA (US)

(73) Assignee: RiboMed Biotechnologies, Inc., Carlsbad, CA (US)

( * ) Notice: Subject to any disclaimer, the term of this patent is extended or adjusted under 35 U.S.C. 154(b) by 122 days.

(21) Appl. No.: 12/724,416

(22) Filed: Mar. 15, 2010

(65) Prior Publication Data

US 2010/0233709 A1  Sep. 16, 2010

Related U.S. Application Data

(60) Provisional application No. 61/160,335, filed on Mar. 15, 2009.

(51) Int. Cl.
*C12Q 1/68* (2006.01)
*C12P 19/34* (2006.01)

(52) U.S. Cl. .................. 435/6.12; 435/6.1; 435/6.11

(58) Field of Classification Search .................. None
See application file for complete search history.

(56) References Cited

U.S. PATENT DOCUMENTS

| | | |
|---|---|---|
| 3,996,345 A | 12/1976 | Ullman et al. |
| 4,351,760 A | 9/1982 | Khanna et al. |
| 4,582,788 A | 4/1986 | Erlich |
| 4,683,194 A | 7/1987 | Saiki |
| 4,739,044 A | 4/1988 | Stabinsky |
| 4,757,141 A | 7/1988 | Fung |
| 4,786,600 A | 11/1988 | Kramer et al. |
| 5,130,238 A | 7/1992 | Malek et al. |
| 5,169,766 A | 12/1992 | Schuster et al. |
| 5,194,370 A | 3/1993 | Berninger et al. |
| 5,215,899 A | 6/1993 | Dattagupta |
| 5,246,866 A | 9/1993 | Nasu et al. |
| 5,399,491 A | 3/1995 | Kacian et al. |
| 5,503,979 A | 4/1996 | Kramer et al. |
| 5,508,178 A | 4/1996 | Rose et al. |
| 5,554,516 A | 9/1996 | Kacian et al. |
| 5,571,669 A | 11/1996 | Lu et al. |
| 5,595,891 A | 1/1997 | Rose et al. |
| 5,597,694 A | 1/1997 | Munroe et al. |
| 5,648,211 A | 7/1997 | Fraiser et al. |
| 5,654,142 A | 8/1997 | Kievits et al. |
| 5,654,176 A | 8/1997 | Smith |

(Continued)

FOREIGN PATENT DOCUMENTS

EP  0369775  5/1990

(Continued)

OTHER PUBLICATIONS

"Alul Methyltransferase", New England Biolabs online catalog (viewed at http://www.neb.com/nebecomm/products/productM0220.asp on Jan. 14, 2012).

(Continued)

*Primary Examiner* — Young J Kim
(74) *Attorney, Agent, or Firm* — The Law Office of Jane K. Babin, Professional Corporation; Jane K. Babin

(57) ABSTRACT

The present invention provides methods for detecting biomarkers based on Abscription®, abortive transcription technology. Particularly, the present invention provides bisulfate free methods for detecting methylation of CpG islands from small samples of DNA. The methods are suitable for multiplexing and can be used to analyze multiple CpG islands from a single sample in a short time.

23 Claims, 6 Drawing Sheets

U.S. PATENT DOCUMENTS

| | | | |
|---|---|---|---|
| 5,679,512 | A | 10/1997 | Laney et al. |
| 5,683,879 | A | 11/1997 | Lanev et al. |
| 5,744,308 | A | 4/1998 | Guillou-Bonnici et al. |
| 5,766,849 | A | 6/1998 | McDonough et al. |
| 5,786,462 | A * | 7/1998 | Schneider et al. ........... 536/23.1 |
| 5,824,517 | A | 10/1998 | Cleuziat et al. |
| 5,837,459 | A | 11/1998 | Berg et al. |
| 5,846,723 | A | 12/1998 | Kim et al. |
| 5,849,723 | A | 12/1998 | Phillion et al. |
| 5,858,801 | A | 1/1999 | Brizzolara |
| 5,888,729 | A | 3/1999 | Kacian et al. |
| 5,888,819 | A | 3/1999 | Goelct et al. |
| 5,912,340 | A | 6/1999 | Kutyavin et al. |
| 6,008,334 | A | 12/1999 | Hanna |
| 6,107,037 | A | 8/2000 | Sousa et al. |
| 6,107,039 | A | 8/2000 | Hanna et al. |
| 6,114,519 | A | 9/2000 | Cole |
| 6,251,594 | B1 | 6/2001 | Gonzalgo et al. |
| 6,268,131 | B1 | 7/2001 | Kang et al. |
| 7,226,738 | B2 | 6/2007 | Hanna |
| 7,541,165 | B2 | 6/2009 | Hanna |
| 2002/0168641 | A1 | 11/2002 | Mortensen et al. |
| 2003/0099950 | A1 | 5/2003 | Hanna |
| 2003/0104432 | A1 * | 6/2003 | Xu et al. ........................... 435/6 |
| 2003/0138783 | A1 | 7/2003 | Sukumar et al. |
| 2004/0054162 | A1 | 3/2004 | Hanna |
| 2004/0175724 | A1 | 9/2004 | Hanna |
| 2005/0214796 | A1 | 9/2005 | Hanna |
| 2006/0204964 | A1 | 9/2006 | Hanna |
| 2006/0240460 | A1 | 10/2006 | Pfeifer et al. |
| 2006/0269937 | A1 | 11/2006 | Clark et al. |
| 2007/0026393 | A1 | 2/2007 | Berlin et al. |
| 2008/0124716 | A1 | 5/2008 | Cooney et al. |

FOREIGN PATENT DOCUMENTS

| | | | |
|---|---|---|---|
| EP | 1364069 | | 4/2009 |
| WO | 8901050 | | 2/1989 |
| WO | 9641006 | | 12/1996 |
| WO | 2001025485 | A2 | 4/2001 |
| WO | 03014388 | | 2/2003 |
| WO | 03038042 | A2 | 5/2003 |
| WO | 03044226 | | 5/2003 |
| WO | 03038042 | A3 | 3/2004 |
| WO | 2004096997 | A2 | 11/2004 |
| WO | 2009140666 | A2 | 11/2009 |
| WO | 2009140666 | A3 | 11/2009 |
| WO | 2010009060 | A2 | 1/2010 |
| WO | 2010009060 | A3 | 6/2010 |
| WO | 2010107716 | A2 | 9/2010 |
| WO | 2010107716 | A3 | 3/2011 |

OTHER PUBLICATIONS

"Cloning vector pBR322, complete sequence", GenBank; Accession No. J01749; GI: 208958, Sep. 30, 2008.
"CpG site", Wikipedia, viewed at http://en.wikipedia.org/wiki/CpG_site, Jan. 16, 2012.
"Dam and Dcm Methylases of *E. coli*", (viewed at http://www.neb.com/nebecomm/tech_reference/restriction_enzymes/dam_dcm_methylases_of_ecoli.asp on Jan. 14, 2012).
"Demethylase", Wikipedia (viewed at http://en.wikipedia.org/wiki/Demethylase on Jan. 16, 2012).
"EcoRI Methyltransferase", New England Biolabs online catalog (viewed at http://www.neb.com/nebecomm/products/productM0211.asp on Jan. 14, 2012).
"Glutathione S-transferase", Wikipedia (viewed at http://en.wikipedia.org/wiki/Glutathione_S-transferase on Dec. 17, 2011).
"GST Gene Fusion System Handbook", GE Healthcare, 18-1157-58 AB (downloaded from http://www.gelifesciences.com/aptrix/upp01077.nsf/Content/Products?OpenDocument&parentid=976038&moduleid=164393&zone=Proteomics on Dec. 17, 2011).
"HaeIII Methyltransferase", New England Biolabs online catalog (viewed at http://www.neb.com/nebecomm/ products/productM0224.asp on Jan. 14, 2012).
"MBD2", HUGO Gene Nomenclature Committee Report on (viewed at http://www.genenames.org/data/hgnc_data.php?hgnc_id=6990 on Dec. 17, 2011).
"MBD2", National Center for Biotechnology Information Gene Report (viewed at http://www.ncbi.nlm.nih.gov/gene/8932 on Dec. 17, 2011).
"MECP2", HUGO Gene Nomenclature Committee Report (viewed at http://www.genenames.org/data/hgnc_data.php?hgnc_id=6990 on Dec. 17, 2011).
"MeCP2", National Center for Biotechnology Gene Report for MECP2 (viewed at http://www.ncbi.nlm.nih.gov/gene/4204 on Dec. 17, 2011).
"MECP2", Wikipedia (viewed at http://en.wikipedia.org/wiki/MECP2 on Dec. 17, 2011).
"Methyl CpG binding protein 2 (Rett syndrome) (MECP2)", UniGene (viewed at http://www.ncbi.nlm.nih.gov/UniGene/clust.cgi?ORG=Hs&CID=200716&ALLPROT=1 on Jan. 16, 2012).
"Methyl-CpG binding domain protein 1 (MBD1)", UniGene (viewed at http://www.ncbi.nlm.nih.gov/UniGene/clust.cgi?ORG=Hs&CID=405610&ALLPROT=1on Jan. 16, 2012).
"Methyl-CpG binding domain protein 2 (MBD2)",, UniGene (viewed at http://www.ncbi.nlm.nih.gov/UniGene/clust.cgi?ORG=Hs&CID=25674&ALLPROT=1 on Jan. 16, 2012).
"Methyl-CpG binding domain protein 4 (MBD4)", UniGene (viewed at http://www.ncbi.nlm.nih.gov/UniGene/clust.cgi?ORG=Hs&CID=35947&ALLPROT=1 on Jan. 16, 2012).
"Methyl-CpG-binding domain protein 2", Wikipedia (viewed at http://en.wikipedia.org/wiki/MBD2on Dec. 17, 2011).
"Methyl-CpG-Binding Domain Protein 2; MBD2", OMIM 603547 (Online Mendelian Inheritance in Man, entry 603547, viewed at http://omim.org/entry/603547 on Dec. 17, 2011).
"Methyl-CpG-Binding Protein 2; MECP2", OMIM 300005 viewed at http://omim.org/entry/300005, Dec. 17, 2011.
"Methytransferase", Wikipedia (viewed at http://en.wikipedia.org/wiki/Methyltransferase on Dec. 16, 2011).
"Protein Domain", Wikipedia (viewed at http://en.wikipedia.org/wiki/Protein_domain on Dec. 17, 2011).
"UniGene Homepage", UniGene (viewed at http://www.ncbi.nlm.nih.gov/unigene on Jan. 16, 2012).
Adorjan et al., "Tumour class prediction and discovery by microarray-based DNA methylation analysis", Nucleic Acids Res. 30: e21, 2002.
Agrawal et al., "Site-specific functionalization of oligodeoxynucleotides for attaching two different reporter groups", Nucleic Acids Res. 18, 1990, 5419-5423.
Aiyar et al., "A Mismatch Bubble in Double-stranded DNA Suffices to Direct Precise Transcription Initiation by *Escherichia coli* RNA Polymerase", J. Biol. Chem. vol. 269, No. 18, 1994, 13179-131.
Akiyama et al., "Cell-Type-Specific Repression of the Maspin Gene is Disrupted Frequently by Demethylation at the Promoter Region in Gastric Intestinal Metaplasia and Cancer Cells", Am J Pathology, vol. 163, No. 5, 2003, 1911-1919.
Alaminos et al., "Clustering of Gene Hypermethylation Associated With Clinical Risk Groups in Neuroblastoma.", Journal of the National Cancer Institute, vol. 96, No. 16, 2004, 1208-19.
Antequera et al., "Number of CpG islands and genes in human and mouse", Proc. Natl. Acad. Sci. USA, vol. 90, 1993, 11995-11999.
Badal et al., "CpG Methylation of Human Papillomavirus Type 16 DNA in Cervical Cancer Cell Lines and in Clinical Specimens: Genomic Hypomethylation Correlates with Carcinogenic Progression", Journal of Virology, vol. 77 No. 11, 2003, 6227-6234.
Ballestar et al., "Methyl-CpG-binding proteins Targeting specific gene repression", Eur. J. Biochem. 268, 2001, 1-6.
Barletta et al., "Reversal of loss of imprinting in tumor cells by 5-aza-2'-deoxycytidine.", Cancer Res 57, 1997, 48-50.
Belinsky et al., "Aberrant CpG island methylation of the $p^{16INK4a}$ and estrogen receptor genes in rat lung tumors induced by particulate carcinogens" Carcinogenesis vol. 23, No. 2, 2002, 335-9.
Belinsky et al., "Promoter hypermethylation of multiple genes in sputum precedes lung cancer incidence in a high-risk cohort", Cancer Res 66:(6), 2006, 3338-44.
Bhattacharya et al., "A mammalian protein with specifc demethylase activity for mCpG DNA", Nature 397, 1999, 579-83.

Boeke et al., "The Minimal Repression Domain of MBD2b Overlaps with the Methyl-CpG-binding Domain and Binds Directly to Sin3A", Journal of Biological Chemistry, vol. 275, No. 45, 2000, 34963-7.

Brock et al., "Prognostic importance of promoter hypermethylation of multiple genes in esophageal adenocarcinoma[1]", Clinical Cancer Research, vol. 9, 2003, 2912-9.

Cairns et al., "Molecular detection of prostate cancer in urine by GSTP1 hypermethylation[1]", Clinical Cancer Research, vol. 7, 2001, 2727-30.

Callahan et al., "Frequent Mutations in Breast Cancer", Ann. N.Y. Acad. Sci. 698, 1993, 21-30.

Chamberlin, "Bacterial DNA-Dependent RNA Polymerases", in The Enzymes, Boyer P.D., ed. Academic Press, New York, N.Y., 1982, 61, 84-86.

Chan et al., "Hypermethylation of multiple genes in tumor tissues and voided urine in urinary bladder cancer patients", Clinical Cancer Research 8, 2002, 46470.

Cheng et al., "Inhibition of DNA Methylation and Reactivation of Silenced Genes by Zebularine", Journal of the National Cancer Inst. vol. 95, No. 5, 2003, 399-409.

Cheung et al., "A Resource of Mapped Human Bacterial Artificial Chromosome Clones", Genome Research, 1999, 983-993.

Cho et al., "Hypomethylation of the MN/CA9 promoter and upregulated MN/CA9 expression in human renal cell carcinoma.", Br J Cancer 85, 2001, 563-7.

Christmann et al., "Acquired resistance of melanoma cells to the antineoplastic agent fotemustine is caused by reactivation of the DNA repair gene MGMT.", Int J Cancer 92, M, 2001, 123-9.

Cifone et al., "Increasing metastatic potential is associated with increasing genetic instability of clones isolated from murine neoplasms", Proc. Natl. Acad. Sci. USA 78, 1981, 6949-6952.

Clarke et al., "S-Adenosylmethionine-Dependent Methyltransferases", in Homocysteine in Health and Disease, Carmel & Jacobsen, eds (Cambridge University Press)., 2001, 63-78.

Claus et al., "Epigenetic targets in hematopoietic malignancies.", Oncogene 22, 2003, 6489-96.

Costas et al., "RNA-protein crosslinking to AMP residues at internal positions in RNA with a new photocrosslinking ATP analog", Nucleic Acids Res. 23, 2000, 1849-1858.

Cunningham et al., "Hypermethylation of the hMLH1 promoter in colon cancer with microsatellite instability", Cancer Res 58, 1998, 3455-60.

Daube et al., "Coupling of RNA displacement and intrinsic termination in transcription from synthetic RNA DNA bubble duplex constructs", Proc. Natl Acad. Set USA 91, 1994, 9539-9543.

Daube et al., "Functional Transcription Elongation Complexes from Synthetic RNA-DNA Bubble Duplexes", Science 258, 1992, 1320-1324.

De Smet et al., "The activation of human gene MAGE-1 in tumor cells is correlated with genome-wide demethylation.", Proc Natl Acad Sci U S A 93:, 1996, 7149-53.

Deitch, et al., "Promoter-specific Activation and Demethylation by MBD2/Demethylase", J Biol Chem. 277, 2002, 35791-4.

Dhasarathy et al., "The MBD protein family—reading an epigenetic mark?", Mutat Res. 647, 2008, 39-43.

Dissinger et al., "Active site labeling of *Escherichia coli* transcription elongation complexes with 5-[4-azidophenacyl)thio)uridine 5'-triphosphate", J Biol Chem 265, S, 1990, 7662-8.

Dulaimi et al., "Clin Cancer Res 10", Detection of bladder cancer in urine by a tumor suppressor gene hypermethylation panel, 2004, 1887-93.

Dunn et al., "Complete Nucleotide Sequence of Bacteriophage T"7 DNA and the Locations of T7 Genetic Elements", J. Mol. Biol. 166, 1982, 477-535.

Eads et al., "MethyLight: a high-throughput assay to measure DNA methylation", Nucleic Acids Res 28, 2000, e32.

Ehrich et al., "A new method for accurate assessment of DNA quality after bisulfite treatment", Nucleic Acids Res 35, 2007, e29.

Esteller et al., "A gene hypermethylation profile of human cancer", Cancer Res 61, 2001, 3225-9.

Esteller, "CpG island hypermethylation and tumor suppressor genes: a booming present, a brighter future.", Oncogene 21, 2002, 5427-40.

Esteller et al., "Hypermethylation-associated Inactivation of the Cellular Retinol-Binding-Protein 1 Gene in Human Cancer", Cancer Res 62, 2002, 5902-5.

Esteller et al., "Promoter Hypermethylation and BRCA1 inaccivation in Sporadic Breast and Ovarian Tumors", J. Natl. Cancer Inst. 52, 2000, 564-569.

Fraga et al., "The affnity of different MBD proteins for a specifc methylated locus depends on their intrinsic binding properties", Nucl. Acids Res, 31, 2003, 1765-1774.

Frommer et al., "A genomic sequencing protocol that yields a positive display of 5-methylcytosine residues in individual DNA strands", Proc. Natl Acad. Sci. USA 39, 1992, 1827-1831.

Gait, "An Introduction to Modern Methods of DNA Synthesis", in Oligonucleotide synthesis: a practical approach, Gait, M.J., ed., Oxford University Press, Oxford, Great Britain, 1984, 1-22.

Gait et al., "Oligoribonucleotide synthesis", in Oligonucleotides and Analogues, 1992, 25-31.

Gama-Sosa et al., "The 5-methylcytosine content of DNA from human tumors", Nucleic Acids Res vol. 11, No. 19, 1983, 6883-94.

Gebhard et al., "Rapid and sensitive detection of CpG-methylation using methyl-binding (MB)-PCR.", Nucleic Acids Res vol. 34, No. 11, 2006, e82.

Geider et al., "An RNA transcribed from DNA at the origin of phage fd single strand to replicative form conversion", Proc. Natl. Acad. Sci. USA vol. 75, No. 2, 1978, 645-649.

Giusti et al., "Synthesis and Characterization of 5'-Fluorescent-dye-labeled Oligonucleotides", PCR Methods Appl. 2, 1993, 223-227.

Gonzalez-Zulueta et al., "Methylation of the 5' CpG island of the p16/CDKN2 tumor suppressor gene in normal and transformed human tissues correlates with gene silencing", Cancer Res 55, 1995, 4531-5.

Gonzalgo et al., "Molecular profiling and classification of sporadic renal cell carcinoma by quantitative methylation analysis.", Clin Cancer Res 10, 2004, 7276-83.

Graff et al., "E-cadherin expression is silenced by DNA hypermethylation in human breast and prostate carcinomas", Cancer Res 55, 1995, 5195-9.

Graff et al., "Methylation patterns of the E-cadherin 5' CpG island are unstable and reflect the dynamic, heterogeneous loss of E-cadherin expression during metastatic progression.", J Biol Chem vol. 275, No. 4, 2000, 2727-32.

Graziano et al., "Prognostic analysis of E-cadherin gene promoter hypermethylation in patients with surgically resected, node-positive, diffuse gastric cancer.", Clin Cancer Res 10, 20047, 2784-9, (2004).

Guatelli et al., "isothermal, in vitro amplification of nucleic acids by a multienzyme reaction modeled after retroviral replication", Proc. Natl. Acad. Sci. USA 87, 1990, 1874-1878.

Gupta et al., "A general method for the synthesis of 3'-sulfhydryl and phosphate group containing oligonucleotides", Nucleic Acids Res vol. 19, No. 11, 1991, 3019-3025.

Gurevich et al., "Preparative in Vitro mRNA Synthesis Using SP6 and T7 RNA Polymerases", Anal. Biochem. 195, 1991, 207-213.

Hanna, "Photoaffinity Cross-Linking Methods for Studying RNA-Protein Interactions", Methods Enzymol. 180, 1989, 383-409.

Hanna et al., "Probing the environment of nascent RNA in *Escherichia coli* transcription elongation complexes utilizing a new fluorescent ribonucleotide analog", Nucleic Acids Res 27, 1999, 1369-1376.

Hanna et al., "Synthesis and characterization of a new photocrosslinking CTP analog and its use in photoaffinity labeling *E.coli* and T7 RNA polymerases", Nucleic Acids Res vol. 21, No. 21, 1993, 2073-2079.

Hanna et al., "Topography of transcription: Path of the leading end of nascent RNA through the *Escherichia coli* transcription complex", Proc. Natl Acad. Sci. USA 80, 1983, 4238-4242.

He et al., "Preparation of probe-modified RNA with 5-mercapto-UTP for analysis of protein-RNA interactions", Nucleic Acids Res. vol. 23, No. 7, 1995, 1231-1238.

Herman et al., "Distinct patterns of inactivation of p15$^{INK4B}$ and p16$^{INK4A}$ characterize the major types of hematological malignancies", Cancer Res 57, 1997, 837-41.

Herman et al., "Inactivation of the CDKN2/p16/MTS1 Gene is Frequently Associated with Aberrant DNA Methylation in AH Common Human Cancers", Cancer Res. 55, 1995, 4525-4530.

Herman et al., "Incidence and functional consequences of hMLH1 promoter hypermethylation in colorectal carcinoma", Proc. Natl. Acad Sci USA 35, 1998, 6870-6875.

Herman et al., "Methylation-specific PCR: a novel PCR assay for methylation status of CpG islands", Proc Natl Acad Sci U S A. 93, 1996, 9821-6.

Herman, "Silencing of the VHL tumor-suppressor gene by DNA methylation in renal carcinoma.", Proc Natl Acad Sci U S A 91, 1994, 9700-4.

Hoque et al., "Quantitation of promoter methylation of multiple genes in urine DNA and bladder cancer detection", J Natl Cancer Inst. 98, 2006, 996-1004.

Hoque et al., "Quantitative detection of promoter hypermethylation of multiple genes in the tumor, urine, and serum DNA of patients with renal cancer", Cancer Res 64, 2004, 5511-7.

Horii et al., "Frequent Replication Errors at Microsatellite Loci in Tumors of Patients with Multiple Primary Cancers", Cancer Res. 54, 1994, 3373-3375.

Iravani et al., "Methylation of the multi tumor suppressor gene-2 (MTS2, CDKN1, p15INK4B) in childhood acute lymphoblastic leukemia", Oncogene 15, 1997, 2609-14.

Issa et al., "Methylation of the oestrogen receptor CpG island links ageing and neoplasia in human colon", Nat. Genet. 7, 1994, 536-540.

Jahr et al., "DNA fragments in the blood plasma of cancer patients: quantitations and evidence for their origin from apoptotic and necrotic cells.", Cancer Res 61, 2001, 1659-65.

Jeronimo, "A quantitative promoter methylation profile of prostate cancer.", Clin Cancer Res 10, 2004, 8472-8.

Jin, "An *Escherichia coli* RNA Polymerase Defective in Transcription due to its Overproduction of Abortive Initiation Products", J. Mol. Biol—236, 1994, 72-80.

Kang et al., "CpG island methylation in premalignant stages of gastric carcinoma.", Cancer Res 61, 2001, 2847-51.

Kinsella et al., "RNA Polymerase: Correlation Between Transcript Length, Abortive Product Synthesis, and Formation of a Stable Ternary Complex", Biochemistry 27, 1982, 2719-2723.

Kwoh et al., "Transcription-based amplification system and detection of amplified human immunodeficiency virus type 1 with a bead-based sandwich hybridization format", Proc. Natl. Acad. Sci. USA 86, 1989, 1173-1177.

Langer et al., "Enzymatic synthesis of biotin-labeled polynucleotides: Novel nucleic acid affinity probes", Proc. Nad. Acad. Scl. USA vol. 78, No. 11, 1981, 6633-6637.

Lee et al., "Aberrant CpG island hypermethylation along multistep hepatocarcinogenesis.", Am J Pathol vol. 163, No. 4, 2003, 1371-8.

Lewis et al., "Transcription of Simian Virus 40 DNA by Wheat Germ RNA Polymerase II", J. Biol. Chem. 255, 1980, 4928-4936.

Lin et al., "Genome-wide hypomethylation in hepatocellular carcinogenesis", Cancer Res 61, 2001, 4238-43.

Loeb et al., "Mutator Phenotype May Be Required for Multistage Carcinogenesis", Cancer Res. 52, 1991, 3075-3079.

Mancini et al., "Constitutively Methylated CpG Dinucleotides as Mutation Hot Spots in the Retinoblastoma Gene (RB1)", Am J. Human Genet 61, 1997, 80-87.

Marras et al., "Genotyping single nucleotide polymorphisms with molecular beacons", In Kwok (ed), Single nucleotide polymophisms: methods and protocols. (The Human Press Inc., Totowa, NJ) vol. 212, 2003, 111-128.

Martin et al., "Processivity in Early Stages of Transcription by T7 RNA Polymerase", Biochemistry 27, 1988, 3966-3974.

Maruyama et al., "Aberrant promoter methylation profile of bladder cancer and its relationship to clinicopathological features", Cancer Res 61, 2001, 8659-63.

Meinkoth et al., "Hybridization of Nucleic Acids Immobilized on Solid Supports", Anal. Blochem. 138, 1984, 267-284.

Meyer et al., "Synthesis and Characterization of a New 5-Thiol-Protected Deoxyuridine Phosphoramidite for Site-Specific Modification of DNA", Bioconjugate Chem. 7, 1996, 401-412.

Milligan et al., "Synthesis of Small RNAs Using T7 RNA Polymerase", Methods Enzymol. 180, 1989, 51-62.

Montemagno et al., "Constructing nanomechanical devices powered by biomolecular motors", Nanotechnology 10, IOP Publishing Ltd., 1999, 225-231.

Mullis et al., "Specific Enzymatic Amplification of DNA In Vitro: The Polymerase Chain Reaction", Cold Spring Harb. Symp. Quant. Biol. 51, 1986, 263-273.

Mullis et al., "The Polymerase Chain Reaction: Why It Works", in Polymerase Chain Reaction, eds., Cold Spring Harbor Laboratory Press, Cold Spring Harbor, N.Y., 1989, 237-243.

Nelson et al., "Bifunctional oligonucleotide probes synthesized using a novel CPG support are able to detect single base pair mutations", Nucleic Acids Res. 17, 1989, 7187-7194.

Ng et al., "Frequent hypermethylation of p16 and p15 genes in multiple myeloma", Blood vol. 89, No. 7, 1997, 2500-6.

Ng et al., "MBD2 is a transcriptional repressor belonging to the MeCP1 histone deacetylase complex", Nature Genetics 23, 1999, 58-61.

Nowell et al., "The Clonal Evolution of Tumor Cell Populations", Science 194, 1976, 23-28.

Palmisano et al., "Predicting Lung Cancer by Detecting Aberrant Promoter Methylation in Sputum", Cancer Res. 50, 2000, 5954-5958.

Patel et al., "A single highly mutable catalytic site amino acid is critical for DNA polymerase fidelity", J Biol Chem vol. 276, No. 7, 2001, 5044-51.

Paz et al., "A systematic profile of DNA methylation in human cancer cell lines", Cancer Res 63, 2003, 1114-21.

Picketts et al., "Differential termination of primer extension: a novel, quantifiable method for detection of point mutations", Human Genetics 89, 1992, 155-157.

Radlowski et al., "Effect of disulfide and sulfhydryl reagents on abortive and productive elongation catalyzed by *Escherichia coli* RNA polymerase", Acta Biochim. Pol. vol. 41, No. No. 4, 1994, 415-419.

Rauch et al., "Methylated-CpG island recovery assay: a new technique for the rapid detection of methylated-CpG islands in cancer", Lab. Invest. 85, 2005, 1172-1180.

Rice et al., "Aberrant methylatton of the BRCAI CpG island promoter is associated with decreased BRCA1 mRNA in sporadic breast cancer cells", Oncogene 17, 1998, 1807-1812.

Robertson, "DNA methylation, methyltransferases, and cancer", Oncogene 20, 2001, 3139-3155.

Rosas et al., "Promoter hypermethylation patterns of p16, $O^6$-methylguanine-DNA-methyltransferase, and death-associated protein kinase in tumors and saliva of head and neck cancer patients", Cancer Res 61, 2001, 939-42.

Saiki et al., "Primer-Directed Enzymatic Amplification of DNA with a Thermostable DNA Polymerase", Science 239, 1988, 481-491.

Sakai et al., "Allele-specific hypermethylation of the retinoblastoma tumor-suppressor gene", Am J Hum Genet 48, 1991, 880-8.

Sanchez-Cespedes et al., "Gene promoter hypermethylation in tumors and serum of head and neck cancer patients.", Cancer Res 60, 2000, 892-5.

Sasaki et al., "Transcriptional sequencing: A method for DNA sequencing using RNA polymerase", Proc Natl Acad Sci USA 95, 1998, 3455-3460.

Sato et al., "Aberrant methylation of the HPP1 gene in ulcerative colitis-associated colorectal carcinoma", Cancer Res 62, 2002, 6820-2.

Sato et al., "Frequent hypomethylation of multiple genes overexpressed in pancreatic ductal adenocarcinoma", Cancer Res 63, 2003, 4158-66.

Shames et al., "A genome-wide screen for promoter methylation in lung cancer identifies novel methylation markers for multiple malignancies.", PLoS Med vol. 3, No. 2, 2006, e486.

Shen et al., "Optimizing annealing temperature overcomes bias in bisulfite PCR methylation analysis", Biotechniques vol. 42, No. 1, 2007, 48-58.

Shibata et al., "Hypermethylation of HPP1 is associated with hMLH1 hypermethylation in gastric adenocarcinomas", Cancer Res 62, 2002, 5637-40.

Singer-Sam et al., "A quantitative HpaII-PCR assay to measure methylation of DNA from a small Number of cells", Nucleic Acids Res vol. 18, No. 3, 1990, 687.

Sinha et al., "Oligonucleotides with reporter groups attached to the 5'-terminus,", in Oligonucleotides and Analogues: A Practical Approach, Eckstein, F., ed., Oxford University Press, 1992, 185-189, 200-201.

Smithies et al., "Detection of Targeted Gene Modifications by Polymerase Chain Reaction", in Polymerase Chain Reaction, eds., Cold Spring Harbor Laboratory Press, Cold Spring Harbor, N.Y., 1989, 199-203.

Spangler et al., "TFIIH action in transcription initiation and promoter escap requires distinct regions of downstream promoter DNA", Proc. Natl. Acad. Set. USA vol. 98, No. 10, 2001, 5544-5549.

Sproat et al., "The synthesis of protected 5'-mercapto-2', 5'-dideoxyribonucleoside-3'-0-phosphoramidites; uses of 5'-mercapto-oligodeoxyribonucleotides", Nucleic Acids Res. vol. 15, No. 15, 1987, 4837-4848.

Tada et al., "MDR1 gene overexpression and altered degree of methylation at the promoter region in bladder cancer during chemotherapeutic treatment", Clin Cancer Res 6, 2000, 4618-27.

Tada et al., "The association of death-associated protein kinase hypermethylation with early recurrence in superficial bladder cancers", Cancer Res 62, 2002, 4048-53.

Takai et al., "Hypomethylation of LINE1 retrotransposon in human hepatocellular carcinomas, but not in surrounding liver cirrhosis.", Jpn J Clin Oncol 30, 2000, 306-9.

Tlsty et al., "Differences in the rates of gene amplification in nontumorigenic and tumorigenic cell lines as measured by Luria-Delbruck fluctuation analysis", Proc. Natl. Acad. Sci. USA 86, 1989, 9441-9445.

Toyota et al., "Aberrant methylation of the Cyclooxygenase 2 CpG island in colorectal tumors", Cancer Res 60, 2000, 4044-8.

Toyota et al., "The role of DNA hypermethylation in human neoplasia", Electrophoresis 21, 2000, 325-333.

Vaish et al., "Expanding the structural and functional diversity of RNA: analog uridine triphosphates as candidates for in vitro selection of nucleic acids", Nucl. Acids Res. 28, 2000, 3316-3322.

Veigl et al., "Biallelic inactivation of hMLH1 by epigenetic gene silencing, a novel mechanism causing human MSI cancers", Proc Natl Acad Sci U S A 95, 1998, 8698-702.

Vogelstein et al., "The multistep nature of cancer", Trends Genet. vol. 9, No. 4, 1993, 138-141.

Walker et al., "Isothermal in vitro amplification of DNA by a restriction enzyme/DNA polymerase system", Proc. Natl. Acad. Sci. USA 59, 1992, 392-396.

Wang et al., "Monovalent cations differ in their effects on transcription initiation from a σ-70 promoter of Escherichia coli", Gene 196, 1997, 95-98.

Warnecke et al., "Detection and measurement of PCR bias in quantitative methylation analysis of bisulphite-treated DNA", Nucleic Acids Res 25:, 1997, 4422-6.

Weisenberger et al., "DNA methylation analysis by digital bisulfite genomic sequencing and digital MethyLight", Nucleic Acids Res vol. 36, No. 2008, 4689-98.

Wiencke et al., "Aberrant methylation of $p16^{INK4a}$ in anatomic and gender-specific subtypes of sporadic colorectal cancer", Cancer Epidemiol Biomarkers Prev 8, 1999, 501-6.

Wu et al., "The Ligation Amplification Reaction (LAR)-Amplification of Specific DNA Sequences Using Sequential Rounds of Template-Dependent Ligation", Genomics 4, 1989, 560-569.

Yegnasubramanian et al., "Combination of methylated-DNA precipitation and methylation-sensitive restriction enzymes (COMPARE-MS) for the rapid, sensitive and quantitative detection of DNA methylation", Nucleic Acids Res vol. 34, No. 3, 2006, e19.

Zeschnigk et al., "A novel real-time PCR assay for quantitative analysis of methylated alleles (QAMA): analysis of the retinoblastoma locus", Nucleic Acids Res 32, 2004, e125.

Zou et al., "Detection of aberrant p16 methylation in the serum of colorectal cancer patients", Clin Cancer Res 8, 2002, 188-91.

Zuckermann et al., "Efficient methods for attachment of thiol specific probes to the 3'-ends of synthetic oligodeoxyribonucleotides", Nucleic Acids Res vol. 15, No. 13, 1987, 5305-5321.

Zuker, "Mfold web server for nucleic acid folding and hybridization prediction", Nucleic Acids Res vol. 31, No. 13, 2003, 3406-15.

* cited by examiner

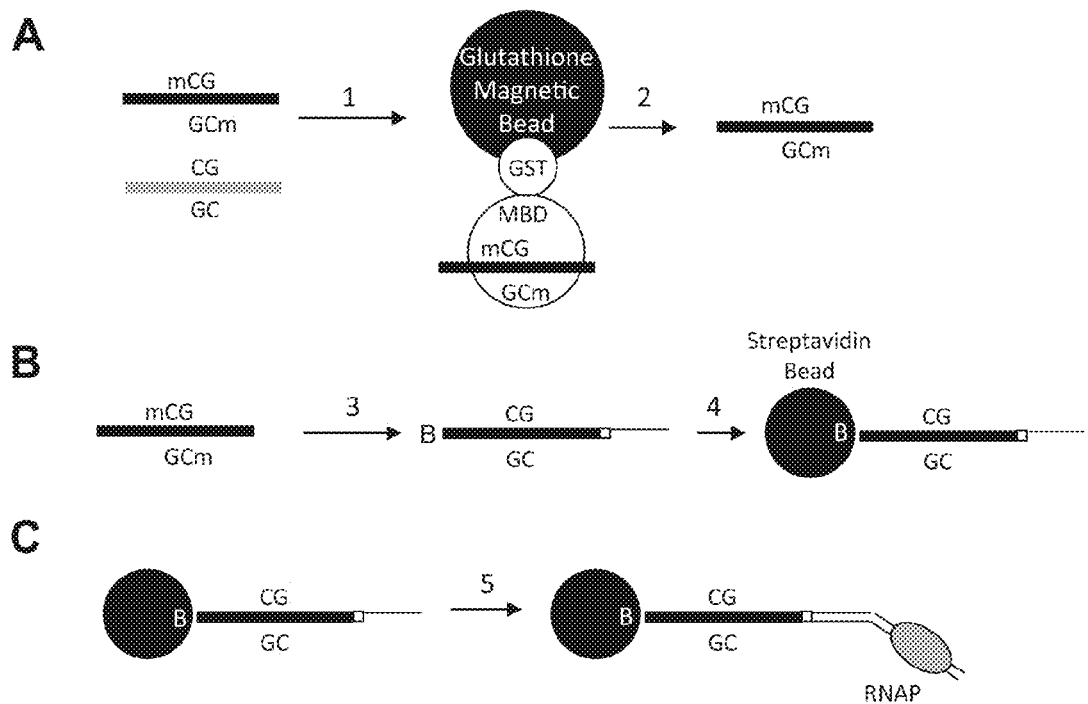
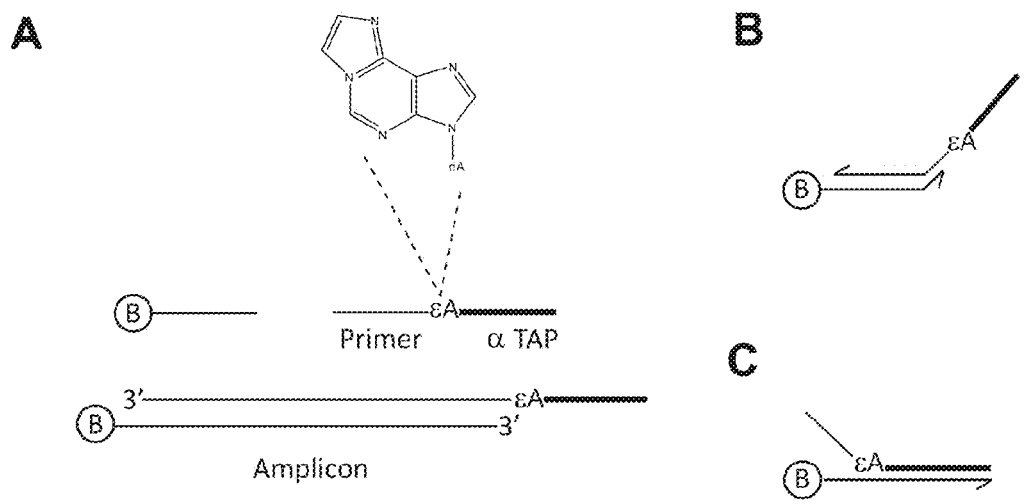
Figure 7

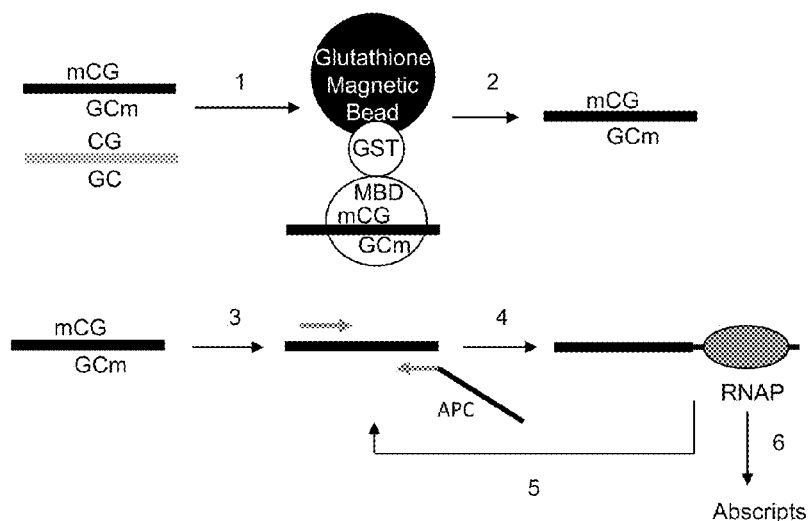
Figure 10
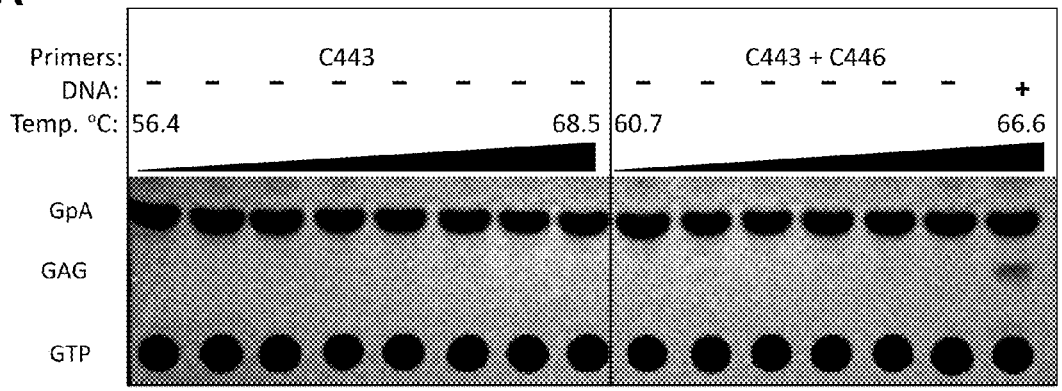
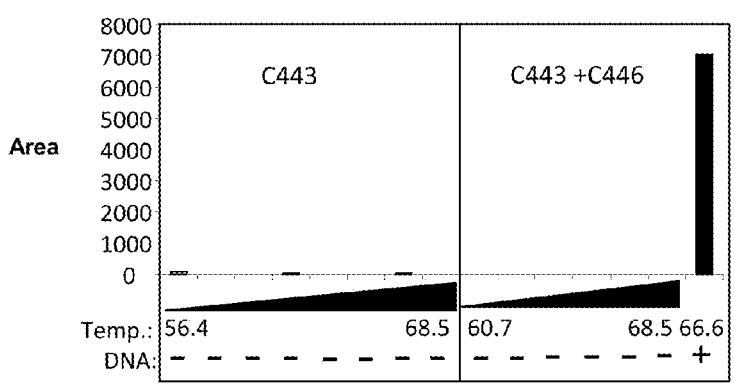
Figure 11

SEQUENCE LISTING

```
<160> NUMBER OF SEQ ID NOS: 50

<210> SEQ ID NO 1
<211> LENGTH: 17
<212> TYPE: PRT
<213> ORGANISM: Artificial Sequence
<220> FEATURE:
<223> OTHER INFORMATION: synthetic peptide

<400> SEQUENCE: 1

Leu Val Pro Arg Gly Ser Pro Gly Ile Ser Gly Gly Gly Gly Gly Ile
1               5                   10                  15

Arg

<210> SEQ ID NO 2
<211> LENGTH: 70
<212> TYPE: PRT
<213> ORGANISM: Mus musculus

<400> SEQUENCE: 2

Glu Ser Gly Lys Arg Met Asp Cys Pro Ala Leu Pro Pro Gly Trp Lys
1               5                   10                  15

Lys Glu Glu Val Ile Arg Lys Ser Gly Leu Ser Ala Gly Lys Ser Asp
            20                  25                  30

Val Tyr Tyr Phe Ser Pro Ser Gly Lys Lys Phe Arg Ser Lys Pro Gln
        35                  40                  45

Leu Ala Arg Tyr Leu Gly Asn Ala Val Asp Leu Ser Ser Phe Asp Phe
    50                  55                  60

Arg Thr Gly Lys Met Met
65                  70

<210> SEQ ID NO 3
<211> LENGTH: 16
<212> TYPE: DNA
<213> ORGANISM: Artificial Sequence
<220> FEATURE:
<223> OTHER INFORMATION: synthetic oligonucleotide primer

<400> SEQUENCE: 3
gcgggaccct ccagaa                                                   16

<210> SEQ ID NO 4
<211> LENGTH: 20
<212> TYPE: DNA
<213> ORGANISM: Artificial Sequence
<220> FEATURE:
<223> OTHER INFORMATION: synthetic oligonucletide primer

<400> SEQUENCE: 4
actcactggt ggcgaagact                                               20

<210> SEQ ID NO 5
<211> LENGTH: 25
<212> TYPE: DNA
```

```
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: (1)..(1)
<223> OTHER INFORMATION: fluroscein - adenosine
<220> FEATURE:
<221> NAME/KEY: misc_feature
<222> LOCATION: (25)..(25)
<223> OTHER INFORMATION: Iowa Black FQ quencher - cytosine

<400> SEQUENCE: 5
accaccctta taaggctcgg aggcc                                           25

<210> SEQ ID NO 6
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 6
ggtacgaaaa ggcggaaaga                                                 20

<210> SEQ ID NO 7
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 7
tgtgggaaag ctggaatatc                                                 20

<210> SEQ ID NO 8
<211> LENGTH: 45
<212> TYPE: DNA
<213> ORGANISM: Artificial Sequence
<220> FEATURE:
<223> OTHER INFORMATION: synthetic oligonucleotide primer
<220> FEATURE:
<221> NAME/KEY: misc_feature
<222> LOCATION: (25)..(25)
<223> OTHER INFORMATION: etheno-deoxyadenosine

<400> SEQUENCE: 8
cacaggtcaa aggtcataaa aatgatttcc cataccaagc accgt                     45

<210> SEQ ID NO 9
<211> LENGTH: 17
<212> TYPE: DNA
<213> ORGANISM: Artificial Sequence
<220> FEATURE:
<223> OTHER INFORMATION: synthetic oligonucleotide primer
<220> FEATURE:
<221> NAME/KEY: misc_feature
<222> LOCATION: (1)..(1)
<223> OTHER INFORMATION: biotin-guanine

<400> SEQUENCE: 9
gtcctcctca cactccg                                                    17

<210> SEQ ID NO 10
<211> LENGTH: 34
<212> TYPE: DNA
<213> ORGANISM: Artificial Sequence
<220> FEATURE:
<223> OTHER INFORMATION: synthetic oligonucleotide primer
<220> FEATURE:
```

```
<221> NAME/KEY: misc_feature
<222> LOCATION: (18)..(18)
<223> OTHER INFORMATION: etheno-deoxyadenosine

<400> SEQUENCE: 10
caccgtcgaa tctctccacc gtgtgcccaa gacc                                  34

<210> SEQ ID NO 11
<211> LENGTH: 22
<212> TYPE: DNA
<213> ORGANISM: Artificial Sequence
<220> FEATURE:
<223> OTHER INFORMATION: thetic oligonucleotide primer
<220> FEATURE:
<221> NAME/KEY: misc_feature
<222> LOCATION: (1)..(1)
<223> OTHER INFORMATION: biotin-guanine

<400> SEQUENCE: 11
gtgcctttca ttccatccag cc                                               22

<210> SEQ ID NO 12
<211> LENGTH: 35
<212> TYPE: DNA
<213> ORGANISM: Artificial Sequence
<220> FEATURE:
<223> OTHER INFORMATION: synthetic oligonucleotide primer
<220> FEATURE:
<221> NAME/KEY: misc_feature
<222> LOCATION: (19)..(19)
<223> OTHER INFORMATION: etheno-deoxyadenosine

<400> SEQUENCE: 12
ccaagaagcc acacgacaag cgggaccctc cagaa                                 35

<210> SEQ ID NO 13
<211> LENGTH: 20
<212> TYPE: DNA
<213> ORGANISM: Artificial Sequence
<220> FEATURE:
<223> OTHER INFORMATION: synthetic oligonucleotide primer
<220> FEATURE:
<221> NAME/KEY: misc_feature
<222> LOCATION: (1)..(1)
<223> OTHER INFORMATION: biotin-adenine

<400> SEQUENCE: 13
actcactggt ggcgaagact                                                  20

<210> SEQ ID NO 14
<211> LENGTH: 34
<212> TYPE: DNA
<213> ORGANISM: Artificial Sequence
<220> FEATURE:
<223> OTHER INFORMATION: synthetic oligonucleotide primer
<220> FEATURE:
<221> NAME/KEY: misc_feature
<222> LOCATION: (17)..(17)
<223> OTHER INFORMATION: etheno-deoxyadenosine

<400> SEQUENCE: 14
cctccatccc aaagtaacct ctgctccctc cgaa                                  34

<210> SEQ ID NO 15
<211> LENGTH: 18
<212> TYPE: DNA
<213> ORGANISM: Artificial Sequence
<220> FEATURE:
<223> OTHER INFORMATION: synthetic oligonucleotide primer
<220> FEATURE:
```

```
<221> NAME/KEY: misc_feature
<222> LOCATION: (1)..(1)
<223> OTHER INFORMATION: biotin-cytosine

<400> SEQUENCE: 15
ccgatggcct agacactg                                                        18

<210> SEQ ID NO 16
<211> LENGTH: 42
<212> TYPE: DNA
<213> ORGANISM: Artificial Sequence
<220> FEATURE:
<223> OTHER INFORMATION: synthetic oligonucleotide primer
<220> FEATURE:
<221> NAME/KEY: misc_feature
<222> LOCATION: (22)..(22)
<223> OTHER INFORMATION: etheno-deoxyadenosine

<400> SEQUENCE: 16
gaaaggacta caaaggacag aaggtacgaa aaggcggaaa ga                              42

<210> SEQ ID NO 17
<211> LENGTH: 20
<212> TYPE: DNA
<213> ORGANISM: Artificial Sequence
<220> FEATURE:
<223> OTHER INFORMATION: synthetic oligonucleotide primer
<220> FEATURE:
<221> NAME/KEY: misc_feature
<222> LOCATION: (1)..(1)
<223> OTHER INFORMATION: biotin-thymine

<400> SEQUENCE: 17
tgtgggaaag ctggaatatc                                                      20

<210> SEQ ID NO 18
<211> LENGTH: 43
<212> TYPE: DNA
<213> ORGANISM: Artificial Sequence
<220> FEATURE:
<223> OTHER INFORMATION: synthetic oligonucleotide primer
<220> FEATURE:
<221> NAME/KEY: misc_feature
<223> OTHER INFORMATION: etheno-deoxyadenosine
<220> FEATURE:
<221> NAME/KEY: misc_feature
<222> LOCATION: (21)..(21)
<223> OTHER INFORMATION: etheno-deoxyadenosine

<400> SEQUENCE: 18
cgaaaatgca tctgagtagc aacctccgcc taaaatccct atg                             43

<210> SEQ ID NO 19
<211> LENGTH: 19
<212> TYPE: DNA
<213> ORGANISM: Artificial Sequence
<220> FEATURE:
<223> OTHER INFORMATION: synthetic oligonucleotide primer
<220> FEATURE:
<221> NAME/KEY: misc_feature
<223> OTHER INFORMATION: biotin-guanine

<400> SEQUENCE: 19
ggtatcctgt ccgctcgca                                                       19

<210> SEQ ID NO 20
<211> LENGTH: 89
<212> TYPE: DNA
<213> ORGANISM: Artificial Sequence
<220> FEATURE:
```

<223> OTHER INFORMATION: synthetic oligonucleotide

<400> SEQUENCE: 20 cattttatg acctttgacc tgtgaaattt atgtttgaca gatcttacaa tgcatgctat     60
aataccacta acggtgcttt aaaattccg                                      89

<210> SEQ ID NO 21
<211> LENGTH: 65
<212> TYPE: DNA
<213> ORGANISM: Artificial Sequence
<220> FEATURE:
<223> OTHER INFORMATION: synthetic oligonucleotide

<400> SEQUENCE: 21 cggaattta aagcaccgtt agtggtatta tagcatgcat tgtaagatct gtcaaacata     60
aattt                                                                65

<210> SEQ ID NO 22
<211> LENGTH: 82
<212> TYPE: DNA
<213> ORGANISM: Artificial Sequence
<220> FEATURE:
<223> OTHER INFORMATION: synthetic oligonucleotide

<400> SEQUENCE: 22
gtcgtgtggc ttcttggaaa tttatgtttg acagatctta caatgcatgc tataatacca   60
ctgaaggtga tataaaattc cg                                             82

<210> SEQ ID NO 23
<211> LENGTH: 65
<212> TYPE: DNA
<213> ORGANISM: Artificial Sequence
<220> FEATURE:
<223> OTHER INFORMATION: synthetic oligonucleotide

<400> SEQUENCE: 23 cggaattta tatcaccttc agtggtatta tagcatgcat tgtaagatct gtcaaacata    60
aattt                                                               65

<210> SEQ ID NO 24
<211> LENGTH: 64
<212> TYPE: DNA
<213> ORGANISM: Artificial Sequence
<220> FEATURE:
<223> OTHER INFORMATION: synthetic oligonucleotide

<400> SEQUENCE: 24
tactttggga tggagggctg ctggaggcgg gtataattta gccagcaccg aatagttacg   60
gtcg                                                                64

<210> SEQ ID NO 25
<211> LENGTH: 48
<212> TYPE: DNA
<213> ORGANISM: Artificial Sequence
<220> FEATURE:
<223> OTHER INFORMATION: synthetic oligonucleotide

<400> SEQUENCE: 25
cgaccgtaac tattcggtgc ttagggcagc gccccgcct ccacgagc                 48

<210> SEQ ID NO 26
<211> LENGTH: 85
<212> TYPE: DNA

```
<213> ORGANISM: Artificial Sequence
<220> FEATURE:
<223> OTHER INFORMATION: synthetic oligonucleotide

<400> SEQUENCE: 26
catttttatg acctttgacc tgtggctgtt gacacagaat aaacgctcaa tgtacaatgg    60
gatggagagg tgctttagta gtgtt                                          85

<210> SEQ ID NO 27
<211> LENGTH: 77
<212> TYPE: DNA
<213> ORGANISM: Artificial Sequence
<220> FEATURE:
<223> OTHER INFORMATION: synthetic oligonucleotide

<400> SEQUENCE: 27
ggagagattc gacggtgctg ttgacacaga taaacgctc aatgtacaat gggatggaga     60
ggtgctttag tagtgtt                                                   77

<210> SEQ ID NO 28
<211> LENGTH: 78
<212> TYPE: DNA
<213> ORGANISM: Artificial Sequence
<220> FEATURE:
<223> OTHER INFORMATION: synthetic oligonucleotide

<400> SEQUENCE: 28
gtcgtgtggc ttcttgggct gttgacacag aataaacgct caatgtacaa tgggatggag    60
aggtgcttta gtagtgtt                                                  78

<210> SEQ ID NO 29
<211> LENGTH: 77
<212> TYPE: DNA
<213> ORGANISM: Artificial Sequence
<220> FEATURE:
<223> OTHER INFORMATION: synthetic oligonucleotide

<400> SEQUENCE: 29
tactttggga tggagggctg ttgacacaga taaacgctc aatgtacaat gggatggaga     60
ggtgctttag tagtgtt                                                   77

<210> SEQ ID NO 30
<211> LENGTH: 83
<212> TYPE: DNA
<213> ORGANISM: Artificial Sequence
<220> FEATURE:
<223> OTHER INFORMATION: synthetic oligonucleotide

<400> SEQUENCE: 30
tctgtccttt gtagtccttt cggctgttga cacagaataa acgctcaatg tacaatggga    60
tggagaggtg ctttagtagt gtt                                            83

<210> SEQ ID NO 31
<211> LENGTH: 81
<212> TYPE: DNA
<213> ORGANISM: Artificial Sequence
<220> FEATURE:
<223> OTHER INFORMATION: synthetic oligonucleotide

<400> SEQUENCE: 31
gctactcaga tgcatttttcg gctgttgaca cagaataaac gctcaatgta caatgggatg    60
gagaggtgct ttagtagtgt t                                               81
```

<210> SEQ ID NO 32
<211> LENGTH: 61
<212> TYPE: DNA
<213> ORGANISM: Artificial Sequence
<220> FEATURE:
<223> OTHER INFORMATION: synthetic oligonucleotide

<400> SEQUENCE: 32
aacactacta aagcacctct ccatcccatt gtacattgag cgtttattct gtgtcaacag    60
c                                                                    61

<210> SEQ ID NO 33
<211> LENGTH: 60
<212> TYPE: DNA
<213> ORGANISM: Artificial Sequence
<220> FEATURE:
<223> OTHER INFORMATION: synthetic oligonucleotide primer

<400> SEQUENCE: 33
agagaatttt ttcataaaca ttaaatgtac aatgggaacg agaaccgtgt gcccaagacc    60

<210> SEQ ID NO 34
<211> LENGTH: 17
<212> TYPE: DNA
<213> ORGANISM: Artificial Sequence
<220> FEATURE:
<223> OTHER INFORMATION: synthetic oligonucleotide primer

<400> SEQUENCE: 34
ctgcctaggg agagaga                                                   17

<210> SEQ ID NO 35
<211> LENGTH: 63
<212> TYPE: DNA
<213> ORGANISM: Artificial Sequence
<220> FEATURE:
<223> OTHER INFORMATION: synthetic oligonucleotide primer

<400> SEQUENCE: 35
gctgttgaca attaataaac gctcaatgta caatgggact gagactctta ggcttctggt    60
ggc                                                                  63

<210> SEQ ID NO 36
<211> LENGTH: 17
<212> TYPE: DNA
<213> ORGANISM: Artificial Sequence
<220> FEATURE:
<223> OTHER INFORMATION: synthetic oligonucleotide primer

<400> SEQUENCE: 36
cctgtggtgg gcgatgc                                                   17

<210> SEQ ID NO 37
<211> LENGTH: 65
<212> TYPE: DNA
<213> ORGANISM: Artificial Sequence
<220> FEATURE:
<223> OTHER INFORMATION: synthetic oligonucleotide primer

<400> SEQUENCE: 37
tgcgaacctt gactataaaa attcaatgta caatgggacg agaaggtac gaaaaggcgg     60 aaaga                                                                65

<210> SEQ ID NO 38

```
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 38
tgtgggaaag ctggaatatc                                                   20

<210> SEQ ID NO 39
<211> LENGTH: 65
<212> TYPE: DNA
<213> ORGANISM: Artificial Sequence
<220> FEATURE:
<223> OTHER INFORMATION: synthetic oligonucleotide primer

<400> SEQUENCE: 39
gctgttgaca cagttcaaac gctcaatgta aaatgggaca atcacctccg cctaaaatcc        60
ctatg                                                                    65

<210> SEQ ID NO 40
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 40
cttgctgttg tgccgttctg                                                   20

<210> SEQ ID NO 41
<211> LENGTH: 60
<212> TYPE: DNA
<213> ORGANISM: Artificial Sequence
<220> FEATURE:
<223> OTHER INFORMATION: synthetic oligonucleotide primer

<400> SEQUENCE: 41
gctgaagaca cagaataaac gatcaatgta taatgggact gagagcggga ccctccagaa        60

<210> SEQ ID NO 42
<211> LENGTH: 44
<212> TYPE: DNA
<213> ORGANISM: Artificial Sequence
<220> FEATURE:
<223> OTHER INFORMATION: synthetic oligonucleotide primer

<400> SEQUENCE: 42
caggtaaaga tccagaaccc aacatgctcg gagttaatag cacc                         44

<210> SEQ ID NO 43
<211> LENGTH: 19
<212> TYPE: DNA
<213> ORGANISM: Artificial Sequence
<220> FEATURE:
<223> OTHER INFORMATION: synthetic oligonucleotide primer

<400> SEQUENCE: 43
gcgctacctg attcaattc                                                    19

<210> SEQ ID NO 44
<211> LENGTH: 1101
<212> TYPE: DNA
<213> ORGANISM: Homo sapiens

<400> SEQUENCE: 44
```

```
ttaaaaaaat ctgttttgtt ctatgtgatt ttcccatacc aagcaccgtg cccggcacaa      60
gctgggatcc cagtacacat ctcgggacgg aagaaccgtg tttccctaga acccagtcag     120
agggcagctt agcaatgtgt cacaggtggg gcgcccgcgt tccgggcgga cgcactggct     180
ccccggccgg cgtgggtgtg gggcgagtgg gtgtgtgcgg ggtgtgcgcg gtagagcgcg     240
ccagcgagcc cggagcgcgg agctgggagg agcagcgagc gccgcgcaga acccgcagcg     300
ccggcctggc agggcagctc ggaggtgggt gggccgcgcc gccagcccgc ttgcagggtc     360
cccattggcc gcctgccggc cgccctccgc ccaaaaggcg gcaaggagcc gagaggctgc     420
ttcggagtgt gaggaggaca gccggaccga gccaacgccg gggactttgt tccctccgcg     480
gaggggactc ggcaactcgc agcggcaggg tctggggccg gcgcctggga gggatctgcg     540 cccccccactc actccctagc tgtgttcccg ccgccgcccc ggctagtctc cggcgctggc     600
gcctatggtc ggcctccgac agcgctccgg agggaccggg ggagctccca ggcgcccggg     660
actggagact gatgcatgag ggggctacgg aggcgcagga gcggtggtga tggtctggga     720
agcggagctg aagtgccctg gcttttggtg aggcgtgaca gtttatcatg accgtgttca     780
ggcaggaaaa cgtggatgat tactacgaca ccggcgagga acttggcagt ggacagtttg     840
cggttgtgaa gaaatgccgt gagaaaagca ccggcctcca gtatgccgcc aaattcatca     900
agaaaaggag gactaagtcc agccggcggg gtgtgagccg cgaggacatc gagcgggagg     960
tcagcatcct gaaggagatc cagcacccca atgtcatcac cctgcacgag gtctatgaga    1020
acaagacgga cgtcatcctg atcttggaac tcgttgcagg tggcgagctg tttgacttct    1080
tagctgaaaa ggaatctttta a                                              1101

<210> SEQ ID NO 45
<211> LENGTH: 2666
<212> TYPE: DNA
<213> ORGANISM: Homo sapiens

<400> SEQUENCE: 45
ttaagcaaag attatcacca ggcaggctaa acttagcaac cggcttttag ctagaagggc      60 aggggggctgg tgtcaggtta tgctgggcca gcaaagaggc ccgggatccc cctcccatgc    120
acctgctgat gggccaaggc caccccaccc caccccttc cttacaagtg ttcagcaccc      180
tcccatccca cactcacaaa cctggccctc tgccctccta ccagaagaat ggatcccctg     240 tgggagggg caggggacct gttcccaccg tgtgcccaag acctcttttc ccacttttc      300 cctcttcttg actcaccctg ccctcaatat cccccgcgc agccagtgaa agggagtccc      360
tggctcctgg ctcgcctgca cgtcccaggg cggggaggga cttccgccct cacgtcccgc    420
tcttcgcccc aggctggatg gaatgaaagg cacactgtct ctctccctag gcagcacagc     480
ccacaggttt ccaggagtgc ctttgtggga ggcctctggg cccccaccag ccatcctgtc     540
ctccgcctgg ggcccagcc cggagagagc cgctggtgca cacagggccg ggattgtctg     600
ccctaattat caggtccagg ctacagggct gcaggacatc gtgaccttcc gtgcagaaac     660
ctccccctcc ccctcaagcc gcctcccgag cctccttcct ctccaggccc ccagtgccca     720
gtgcccagtg cccagcccag gcctcggtcc cagagatgcc aggagccagg agatggggag     780
ggggaagtgg gggctgggaa ggaaccacgg gccccgccc gaggcccatg ggcccctcct     840
aggcctttgc ctgagcagtc cggtgtcact accgcagagc ctcgaggaga agttccccaa     900
ctttcccgcc tctcagcctt tgaaagaaag aaaggggagg gggcaggccg cgtgcagccg     960
cgagcggtgc tgggctccgg ctccaattcc ccatctcagt cgttcccaaa gtcctcctgt    1020
```

| | | | |
|---|---|---|---|
| ttcatccaag | cgtgtaaggg | tccccgtcct tgactccta gtgtcctgct gcccacagtc | 1080 |
| cagtcctggg | aaccagcacc | gatcacctcc catcgggcca atctcagtcc cttccccct | 1140 |
| acgtcgggc | ccacacgctc | ggtgcgtgcc cagttgaacc aggcggctgc ggaaaaaaaa | 1200 |
| aagcggggag | aaagtagggc | ccggctacta gcggttttac gggcgcacgt agctcaggcc | 1260 |
| tcaagacctt | gggctgggac | tggctgagcc tggcgggagg cggggtccga gtcaccgcct | 1320 |
| gccgccgcgc | cccggttc | tataaattga gcccgcagcc tccgcttcg ctctctgctc | 1380 |
| ctcctgttcg | acagtcagcc | gcatcttctt ttgcgtcgcc aggtgaagac gggcggagag | 1440 |
| aaacccggga | ggctagggac | ggcctgaagg cggcagggc gggcgcaggc cggatgtgtt | 1500 |
| cgcgccgctg | cggggtgggc | ccgggcggcc tccgcattgc aggggcgggc ggaggacgtg | 1560 |
| atgcggcgcg | ggctgggcat | ggaggcctgg tgggaggg gaggggaggc gtgtgtgtcg | 1620 |
| gccgggggcca | ctaggcgctc | actgttctct ccctccgcgc agccgagcca catcgctcag | 1680 |
| acaccatggg | gaaggtgaag | gtcggagtca acgggtgagt tcgcgggtgg ctgggggggcc | 1740 |
| ctgggctgcg | accgccccg | aaccgcgtct acgagccttg cgggctccgg gtctttgcag | 1800 |
| tcgtatgggg | gcagggtagc | tgttccccgc aaggagagct caaggtcagc gctcggacct | 1860 |
| ggcggagccc | cgcacccagg | ctgtggcgcc ctgtgcagct ccgcccttgc ggcgccatct | 1920 |
| gcccggagcc | tccttcccct | agtccccaga acaggaggt ccctactccc gcccgagatc | 1980 |
| ccgacccgga | ccctaggtg | ggggacgctt tctttccttt cgcgctctgc ggggtcacgt | 2040 |
| gtcgcagagg | agccctccc | ccacggcctc cggcaccgca ggccccggga tgctagtgcg | 2100 |
| cagcgggtgc | atccctgtcc | ggatgctgcg cctgcggtag agcggccgcc atgttgcaac | 2160 |
| cgggaaggaa | atgaatgggc | agccgttagg aaagcctgcc ggtgactaac cctgcgctcc | 2220 |
| tgcctcgatg | ggtggagtcg | cgtgtggcgg ggaagtcagg tggagcgagg ctagctggcc | 2280 |
| cgatttctcc | tccgggtgat | gcttttccta gattattctc tggtaaatca aagaagtggg | 2340 |
| tttatggagg | tcctcttgtg | tccctcccc gcagaggtgt ggtggctgtg gcatggtgcc | 2400 |
| aagccgggag | aagctgagtc | atgggtagtt ggaaaaggac atttccaccg caaaatggcc | 2460 |
| cctctggtgg | tggccccttc | ctgcagcgcc ggctcacctc acggcccgc ccttcccctg | 2520 |
| ccagcctagc | gttgacccga | ccccaaaggc caggctgtaa atgtcaccgg gaggattggg | 2580 |
| tgtctgggcg | cctcggggaa | cctgcccttc tccccattcc gtcttccgga aaccagatct | 2640 |
| cccaccgcac | cctggtctga | ggttaa | 2666 |

<210> SEQ ID NO 46
<211> LENGTH: 1975
<212> TYPE: DNA
<213> ORGANISM: Homo sapiens

<400> SEQUENCE: 46

| | | | |
|---|---|---|---|
| ttaaaacaac | agaaacctat | tgtctcacac ttccggggc cagaagtttg aaacccaggt | 60 |
| gtgttaggat | cctgctccct | ctgaaggctc cagggaagag tgtcctctgc tccctccgaa | 120 |
| ggctccaggg | aagggtctgt | cctcttaggc ttctggtggc ttgcaggtgc agccctccaa | 180 |
| tcctcctccc | caagcggcct | tctgcctata aggacacgag tcatactgga tgaggggccc | 240 |
| actaattgat | ggcttctgta | aagtcccat ctccaaataa ggtcacattg tgaggtactg | 300 |
| ggagttagga | ctccaacata | gcttctctgg tggacacaat tcaactccta ataacgtcca | 360 |
| cacaaccca | agcagggcct | ggcacccgt gtgctctctg gagagcggct gagtcaggct | 420 |
| ctggcagtgt | ctaggccatc | ggtgactgca gcccctggac ggcatcgccc accacaggcc | 480 |

```
ctggaggctg cccccacggc ccctgacag ggtctctgct ggtctggggg tccctgacta      540
ggggagcggc accaggaggg gagagactcg cgctccgggc tcagcgtagc cgccccgagc      600
aggaccggga ttctcactaa gcgggcgccg tcctacgacc cccgcgcgct ttcaggacca      660
ctcgggcacg tggcaggtcg cttgcacgcc cgcggactat ccctgtgaca ggaaaaggta      720
cgggccattt ggcaaactaa ggcacagagc tcaggcgga agctgggaag gcgccgcccg      780
gcttgtaccg gccgaaggc catccgggtc aggcgcacag ggcagcggcg ctgccggagg      840
accagggccg gcgtgccggc gtccagcgag gatgcgcaga ctgcctcagg cccggcgccg      900
ccgcacaggg catgcgccga cccggtcggg cgggaacacc ccgcccctcc cgggctccgc      960
cccagctccg ccccgcgcg ccccggcccc gccccgcgc gctctcttgc ttttctcagg     1020
tcctcggctc cgccccgctc tagacccccg cccacgccgc catccccgtg ccctcggcc     1080
ccgccccgc gccccggata tgctgggaca gcccgcgccc ctagaacgct ttgcgtcccg     1140
acgcccgcag gtcctcgcgg tgcgcaccgt ttgcgacttg gtgagtgtct gggtcgcctc     1200
gctcccggaa gagtgcggag ctctcccctcg ggacggtggc agcctcgagt ggtcctgcag     1260
gcgccctcac ttcgccgtcg ggtgtggggc cgccctgacc cccacccatc ccgggcgagc     1320
tccaggtgcg ccccaagtgc ctcccaggtg ttgcccagcc tttccccggg cctggggttc     1380
ctggactagg ctgcgctgca gtgactgtgg actggcgtgt ggcggggggtc gtggcagccc     1440
ctgccttacc tctaggtgcc agccccaggc ccgggccccg ggttcttcct acccttccat     1500
gctgccagct ttccctccgc cagctgctcc aggaagcttc cagaagcccc tgcgcgggcc     1560
ttggcttgca gcaaccctttt agcatactta ggcagagtcc catatttcct tcctgctgga     1620
ggccaagttc taggggcctt ctggttacta tggctggtgt ttgtgtacat catacccctaa     1680
ctgtattcat caacacttag agtaagcaag gctcgctgga gagccacaca cactgggcac     1740
cgtaatgtcg gttataacac cgcagaggag ttctgaacta tgtatttcgc actcctgggt     1800
tcatcatctc ctgaaatctc agggtggtgt ttgctctcag ttgcttcagc tgagtagctg     1860
gctttctgtc ctggaaagca gactttgtac atgtgtgtgc aacctatgcc tgctgagatc     1920
atcatcagac agggaagcgg cttggtccag agagctgttc tcagtagaat gttaa          1975
```

<210> SEQ ID NO 47
<211> LENGTH: 1935
<212> TYPE: DNA
<213> ORGANISM: Homo sapiens

<400> SEQUENCE: 47

```
ttaatacctg ggtgatggga tgatctgtac agcaaaccat catggcgcac acacctatgt       60
aacaaacctg cacatcctct acatgtaccc cagaacttca aataaaagtt ggacggccag      120
gcgtggtggc tcacgcctgt aatcccagca ctttgggaag ccgaggcgtg cagatcacct      180
aaggtcagga gttcgagacc agccggcca acatggtgaa accccgtctc tactaaaaat      240
acaaaaatca gccagatgtg gcacgcacct ataattccac ctactcggga ggctgaagca      300
gaattgcttg aacccgagag gcggaggttg cagtgagccg ccgagatcgc gccactgcac      360
tccagcctgg gccacagcgt gagactacgt cataaaataa aataaaataa cacaaaataa      420
aataaaataa aataaaataa aataaaataa aataaaataa aataaaataa aaaaataaaa      480
taaaataaaa taaaataaag caatttcctt tcctctaagc ggcctccacc cctctcccct      540
gccctgtgaa gcgggtgtgc aagctccggg atcgagcgg tcttagggaa tttccccccg      600
cgatgtcccg gcgcgccagt tcgctgcgca cacttcgctg cggtcctctt cctgctgtct      660
```

| | |
|---|---|
| gtttactccc taggccccgc tgggacctg ggaagagg aaaggcttcc ccggccagct | 720 |
| gcgcggcgac tccgggact ccagggcgcc cctctgcggc cgacgcccgg ggtgcagcgg | 780 |
| ccgccggggc tggggccggc gggagtccgc gggaccctcc agaagagcgg ccggcgccgt | 840 |
| gactcagcac tggggcggag cggggcggga ccacccttat aaggctcgga ggccgcgagg | 900 |
| ccttcgctgg agtttcgccg ccgcagtctt cgccaccagt gagtacgcgc ggcccgcgtc | 960 |
| cccggggatg gggctcagag ctcccagcat ggggccaacc cgcagcatca ggcccgggct | 1020 |
| cccggcaggg ctcctcgccc acctcgagac ccgggacggg ggcctagggg acccaggacg | 1080 |
| tccccagtgc cgttagcggc tttcaggggg cccggagcgc ctcggggagg gatgggaccc | 1140 |
| cggggcggg gagggggc agactgcgct caccgcgcct tggcatcctc ccccgggctc | 1200 |
| cagcaaactt ttctttgttc gctgcagtgc cgccctacac cgtggtctat ttcccagttc | 1260 |
| gaggtaggag catgtgtctg gcagggaagg gaggcagggg ctggggctgc agcccacagc | 1320 |
| ccctcgccca cccggagaga tccgaacccc cttatccctc cgtcgtgtgg cttttacccc | 1380 |
| gggcctcctt cctgttcccc gcctctcccg ccatgcctgc tccccgcccc agtgttgtgt | 1440 |
| gaaatcttcg gaggaacctg tttccctgtt ccctccctgc actcctgacc cctcccggg | 1500 |
| ttgctgcgag gcggagtcgg cccggtcccc acatctcgta cttctccctc cccgcaggcc | 1560 |
| gctgcgcggc cctgcgcatg ctgctggcag atcagggcca gagctggaag gaggaggtgg | 1620 |
| tgaccgtgga gacgtggcag gagggctcac tcaaagcctc ctgcgtaagt gaccatgccc | 1680 |
| gggcaagggg aggggtgct gggccttagg gggctgtgac taggatcggg ggacgcccaa | 1740 |
| gctcagtgcc cctccctgag ccatgcctcc cccaacagct atacgggcag ctcccccaagt | 1800 |
| tccaggacgg agacctcacc ctgtaccagt ccaataccat cctgcgtcac ctgggccgca | 1860 |
| cccttggtga gtcttgaacc tccaagtcca gggcaggcat gggcaagcct ctgccccgg | 1920 |
| agccctttg tttaa | 1935 |

<210> SEQ ID NO 48
<211> LENGTH: 937
<212> TYPE: DNA
<213> ORGANISM: Homo sapiens

<400> SEQUENCE: 48

| | |
|---|---|
| ttaaccttac tcgccccagt ctgtcccgac gtgacttcct cgaccctcta aagacgtaca | 60 |
| gaccagacac ggcggcggcg gcgggagagg ggattccctg cgccccggga cctcagggcc | 120 |
| gctcagattc ctggagagga agccaagtgt ccttctgccc tcccccggta tcccatccaa | 180 |
| ggcgatcagt ccagaactgg ctctcggaag cgctcgggca aagactgcga agaagaaaag | 240 |
| acatctggcg gaaacctgtg cgcctgggc ggtggaactc ggggaggaga gggagggatc | 300 |
| agacaggaga gtgggactac ccccctctgc tcccaaattg gggcagcttc ctgggttccc | 360 |
| gattttctca tttccgtggg taaaaaaccc tgccccacc gggcttacgc aattttttta | 420 |
| aggggagagg aggaaaaat ttgtgggggg tacgaaaagg cggaaagaaa cagtcatttc | 480 |
| gtcacatggg cttggttttc agtcttataa aaaggaaggt tctctcggtt agcgaccaat | 540 |
| tgtcatacga cttgcagtga gcgtcaggag cacgtccagg aactcctcag cagcgcctcc | 600 |
| ttcagctcca cagccagacg ccctcagaca gcaaagccta ccccgcgcc cgcgcctgcc | 660 |
| cgccgctgcg atgctcgccc gcgccctgct gctgtgcgcg gtcctggcgc tcagccatac | 720 |
| aggtgagtac ctggcgccgc gcaccgggga ctccggttcc acgcacccgg gcagagtttc | 780 |
| cgctctgacc tcctgggtct atcccagtac tccgacttct ctccgaatag agaagctacg | 840 |

```
tgacttggga aagagcttgg accgctagag ttcgaaagaa ctccgtggat attccagctt    900
tcccacaagc actgatcatt atgagccagt tacttaa                            937
```

<210> SEQ ID NO 49
<211> LENGTH: 704
<212> TYPE: DNA
<213> ORGANISM: Homo sapiens

<400> SEQUENCE: 49

```
ttaatagcac ctcctccgag cactcgctca cggcgtcccc ttgcctggaa agataccgcg     60
gtccctccag aggatttgag ggacagggtc ggaggggggct cttccgccag caccggagga   120
agaaagagga ggggctggct ggtcaccaga gggtggggcg gaccgcgtgc gctcggcggc   180
tgcggagagg gggagagcag gcagcgggcg gcggggagca gcatggagcc ggcggcgggg   240
agcagcatgg agccttcggc tgactggctg gccacggccg cggcccgggg tcgggtagag   300
gaggtgcggg cgctgctgga ggcggggggcg ctgcccaacg caccgaatag ttacggtcgg   360
aggccgatcc aggtgggtag agggtctgca gcgggagcag gggatggcgg gcgactctgg   420
aggacgaagt ttgcagggga attggaatca ggtagcgctt cgattctccg gaaaaagggg   480
aggcttcctg gggagttttc agaaggggtt tgtaatcaca gacctcctcc tggcgacgcc   540 ctggggggctt gggaagccaa ggaagaggaa tgaggagcca cgcgcgtaca gatctctcga   600
atgctgagaa gatctgaagg ggggaacata tttgtattag atggaagtat gctctttatc   660
agatacaaaa tttacgaacg tttgggataa aaagggagtc ttaa                    704
```

<210> SEQ ID NO 50
<211> LENGTH: 1238
<212> TYPE: DNA
<213> ORGANISM: Homo sapiens

<400> SEQUENCE: 50

```
ttaaaggctg cggactgtgc tactgccccct tctgatgccc cctcctctac acagcaatca    60
ttcagcgtcc cttagtcact ccggacagcg acaggccccg cggccgccat gcccaccgcc   120
tccatgccat gccaccgcc gccatgccta ccgccgccaa agtccaccac cgccatgcct   180
acccgctgcc aatgcccacc gccgccaata cccactgtcg ccgccttccc cctacctccc   240
agccacttcc tacggactct ccccgcgccg cgaccaccaa cacaaccccc accactgtca   300
caccgactca tcccccctggt ccactgccat agcctcctcg cctcggtcac tgcgacgaat   360 tccccccca gtcgccccac gtaccctgct ccaccacgca gtggtcacta ttatacacct   420
acctgcgctc aacaccccct aaataccgat cacttcacgt accttcgccc cgccacaatc   480
actccaatat acctacctcc gcctaaaatc cctatgcact ggtccccca cgtaccctcg   540 ccacacggaa ctgcaatcac cctgatgtac ccacctccac ccatgtccct tgcccactgc   600
ggttaccccg catgctccca gtcaccaccg cccttcccac cgcagacacc cgcaatagga   660
cctgtcgcga caccacagtt gggggcggat ggggacgcg ccccaatgcg agcggacagg   720
ataccatcgg ggcagaacgg cacaacagca agcctctgaa cattccggat ctggttctcc   780
agaacaaagg actttagggc ccaaattccg tttattcagt actccaagtc ctaaaaactt   840
ggaatatctg atgaataaaa gtggccgctc cccaggctgt tcttgagag aagccaccgg   900 cacagctgac cttgcccgct ccatcgcgtc actgaccgct cctcagacag atgcgtcagg   960
catctccggc ggccgctcca ctctgcgcca gactcgctgc agcagcggca ggcttcgcac  1020
acatccccgc ctgagcatgc gcgccagcct gcctctgcgg ccgcgcaggc gtgcttgttt  1080
```

```
gccgcagtgc aggggtccca gctccctccc tcaccggaat gacctggggg gaggggggcta    1140 ctggacccct agggcccccac agcactgttg caatgagagg gggcctctag aaaccataag    1200
caacctggga tcaatggaca tgtctacctg tttttttaa                            1238
```

ABSCRIPTION BASED MOLECULAR DETECTION

RELATED APPLICATION

This application claims the benefit of priority under 35 USC §119 of U.S. Provisional Application Ser. No. 61/160,335 filed Mar. 15, 2009, the entire disclosure of which is incorporated herein by reference.

STATEMENT OF GOVERNMENT SUPPORT

This invention was made, at least in part, with government support under Contract No. HHSN261200900047C from the National Institutes of Health, National Cancer Institute. The Government has certain rights in this invention.

BACKGROUND OF THE INVENTION

Cancer is actively avoided through the expression of numerous tumor-suppressor genes that regulate the cell division cycle and mediate interactions among cells. Studies of benign and malignant tumors have shown that cancer develops through a multi-step process where randomly accumulated changes either enhance the expression of proto-oncogenes or reduce the expression or function of tumor-suppressor and DNA repair genes. Somatic mutations account for some of these changes in tumor-suppressor and DNA repair genes. However, it has recently become apparent that epigenetic changes, such as DNA hypermethylation and hypomethylation, also play a large role in the development of cancer through inactivation or enhancement of tumor suppressors or proto-oncogenes. Hypermethylation of CpG promoter islands occurs at an early stage of cancer development and is found in virtually all tumors, making it potentially very useful as a diagnostic marker, allowing cancer to be noninvasively detected in the early stages when treatment is most effective. For example, hypermethylation of the promoter region of genes such as DAP kinase, p16, and MGMT has reportedly been detected in the sputum of smokers up to 3 years prior to the diagnosis of squamous cell lung carcinoma (Belinsky et al. (2006). Cancer Res. 66:3338-44, Palmisano et al. 2000. Cancer Res. 60:5954-8). Similarly, hypermethylation of a small panel of genes may be a valuable early detection indicator for non-small cell lung cancer. Hypermethylation of a small panel of genes was detected in the early stages of breast cancer but was not detected in normal or benign breast tissue Krassenstein et al. (2004). Clin Cancer Res. 10:28-32.

Methylation of cytosines in CpG islands is an early event in most cancers that leads to reduced expression of many genes, including tumor suppressor genes. Surveys of CpG island methylation in tumor cell DNA suggest that this epigenetic change is common enough to rival the impact of mutation in tumor progression. Early detection of abnormal methylation can lead to regular screening and early diagnosis when treatment is most effective. Early epigenetic changes are often detectable in blood serum or other bodily fluids (urine, sputum, saliva), not just in the tumor tissue itself, which means that epigenetic diagnostic testing can be done noninvasively using these fluids. Diagnostic tests based on CpG island methylation may also be utilized for drug development, identification of patient populations that will respond to these drugs and post treatment monitoring.

Recent improvements in the sensitivity of methylation detection and elucidation of methylation signatures for specific cancers have made it feasible to assay for tumors by sampling DNA from bodily fluids. Tumor cells release DNA into blood from a relatively early stage of the disease. From 3% to over 90% of the DNA in the blood of cancer patients has been found to be of tumor origin (Kim et al. (2004) J. Clin. Oncol. 22:2363-70. The development of PCR-based methylation assays has made it possible to detect the presence of tumors noninvasively from blood, sputum, and urine. In one study methylation detection was more sensitive than urine cytology in detecting aberrant premalignant cells. Clinical sensitivities (the proportion of confirmed cases detected) are typically low in surveys of blood samples using a single methylation marker. However, clinical specificity (the proportion of normal controls that test negative) from blood samples approaches 100%. The clinical sensitivities should increase with methylation tests that assess more than a single CpG island.

The appearance of abnormally methylated DNA in bodily fluids by itself does not help to pinpoint which organ is affected by a tumor. Surprisingly little information is needed to establish the tissue origin of a tumor. Numerous methylation screening studies have established methylation signatures; collections of methylated CpG islands that are strongly associated with cancers from particular organs. In one survey, aberrant methylation of 3 to 4 candidate CpG islands was sufficient to identify from 70-90% of 15 cancer types (Esteller et al. (2001) Cancer Res. 61:3225-9). Methylation profiles developed for primary tumors could be applied to tumor cell lines to accurately identify the tissue origin of their parent tumors (Graziano et al. (2004) Clin. Cancer Res. 10:2784). This result suggests that methylation signatures of different tumor types are not greatly affected by the selective pressures associated with growth in culture. The availability of methylation profiles should greatly enhance the ability to detect cancer in inaccessible organs through a simple blood test.

Detection of methylation in clinical samples would enable early detection of cancer. The development of simple and sensitive multiplex detection assays will allow small clinical samples to be profiled for the status of multiple CpG islands. This kind of information will be valuable in diagnosis and treatment.

Methods for Detecting DNA Methylation

A number of methods have been used to detect methylated-CpG (mCpG) in target DNA. The three primary methods in current use are detailed below.

Bisulfite Methods. The most commonly used methylation detection methods are based on bisulfite modification of DNA, resulting in deamination of cytosine residues to uracil while leaving the methylated cytosines unchanged. Upon PCR amplification, the methylated cytosine is copied to cytosine and uracil is copied to thymine. As a result, the retention of cytosine at a specific position indicates methylation. The modified DNA is then analyzed, e.g. by sequence analysis, methylation-specific PCR (MSP) (Herman et al. (1996) Proc. Natl. Acad. Sci. USA 93:9821-26), or hybridization (e.g. to a microarray or blot). In MSP, a pair of methylation-specific oligonucleotide primers is added to the bisulfite-treated DNA and PCR is performed in order to amplify the target DNA. Fluorescence-based quantitative real-time PCR can also be performed on bisulfite-modified DNA (Eads et al. (2000) Nucl. Acids Res. 28:E32; Zeschnigk et al. (2004) Nucl. Acids Res. 32:e125).

Calibrated, fluorescence-based variants of MSP exploit real-time PCR to provide quantification of the amount of methylated DNA in a sample. An important underlying assumption of these PCR based methods is that the few CpG sites that are recognized by the primers/probes reflect the overall status of the target CpG island. While this is usually true for heavily methylated or completely unmethylated islands, partially methylated targets are probably not readily scored in methylated- or unmethylated-specific reactions.

An advantage of bisulfite modification is that it differentially marks methylated versus unmethylated sites allowing sequencing methods to detect methylation patterns. Sequencing of cloned bisulfite-treated DNA is the most commonly used method for methylation detection. It provides information on the success of the bisulfite treatment in addition to sampling a greater number of CpG sites than the MSP based methods. Due to its complexity and expense, however, bisulfite sequencing is better suited for marker discovery than clinical diagnostics. Bisulfite treatment destroys a large percentage of the input DNA, resulting in limited sensitivity and a requirement for large amounts of DNA. Quality control assessments of bisulfite treated DNA are necessary before performing a detection assay to avoid misleading results. There is a potential of false-positive results for MSP-based assays due to incomplete cytosine deamination during bisulfite treatment. Amplification of bisulfite treated DNA is affected by PCR bias favoring unmethylated DNA. While this problem can usually be corrected by optimizing primer annealing conditions, it may complicate primer design and testing. Template biases can be eliminated with the use of digital bisulfite-PCR. Dilution of the DNA sample to an average of less than one copy per reaction eliminates competition among templates. Individual molecules can be sequenced without biases introduced by cloning.

Commercial kits, reagents and systems employing bisulfite treatment for analyzing mCpG are available. Epigenetics (Berlin) offers two variants of the MethyLight assay, adaptations of quantitative real-time PCR, called Quantitative MethyLight (QM) and Heavy Methyl (HM). QM utilizes Taqman® probes to generate a fluorescent signal. During the course of amplification, the fluor is cleaved from the Taqman® probe resulting in fluorescence that can be detected in real-time (Wojdacz & Dobrovic (2007) Nucl. Acids Res. 35:e41). HM is an adaptation of QM in which blocker oligonucleotides are added to the reaction. These blocker oligonucleotides prevent amplification of unmethylated DNA, resulting in increased assay sensitivity (Cottrell et al. (2004) Nucl. Acids Res. 32:e10). Pyrosequencing® is also utilized for methylation quantification from bisulfite-modified DNA, as exemplified by the Pyro Q-CpG™ system from Biotage (Uppsala, Sweden; Tost et al. (2003) Biotechniques 35:152-56).

Although bisulfite modification is a widely used, the extensive DNA degradation it causes can introduce sampling errors when few molecules are long enough to be amplified (Ehrich et al. (2007) Nucl. Acids Res. 35:e29). Furthermore, the assays are time-consuming, require a harsh base denaturation step, and have a high-probability of false-positive results due to incomplete cytosine deamination during bisulfite treatment.

Methylation-Sensitive Restriction Enzyme Digestion Methods. A second type of method for detecting mCpG in DNA relies on differential cleavage by restriction endonucleases. DNA is treated with either a MSRE (methylation-sensitive restriction endonuclease) or a MDRE (methylation dependent restriction endonuclease), amplified and then analyzed by microarray or gel electrophoresis. MSREs such as HpaII and AciI cut a DNA sequence only if it is unmethylated. MDREs are restriction endonuclease that require methylation of a DNA sequence for cleavage. By treating a sample of DNA with either of these enzymes and subsequent comparison to a control sample, the methylation state of the DNA sample can be determined. If digestion of a specific DNA sample occurs after treatment with a MDRE, then the DNA can be assumed to be methylated. Conversely, if the DNA is uncut when treated with a MSRE, then the sample can be assumed to be methylated. By comparing the amount of cut versus uncut DNA, the level of methylation can be estimated. A common read-out for this type of methylation analysis is the subsequent amplification and fluorescent labeling of the digested DNA. The fragments can then be hybridized to a library microarray and analyzed or simply resolved by electrophoresis.

Commercially available restriction endonuclease-based systems include Orion's MethylScope, which utilizes a microarray read-out (Lippman et al. (2004) Nature 430:471-76), and MethyScreen, which employs quantitative real-time PCR (Ordway et al. (2006) Carcinogenesis 27:2409-23).

An advantage of MSRE/MDRE digestion is that no pretreatment of the DNA is necessary, although it is often performed in conjunction with bisulfite treatment of DNA in a procedure called COBRA (Xiong & Laird (1997) Nucl. Acids Res. 25:2532-34). Some disadvantages with this procedure are that it is lengthy and is dependent on the presence of MSRE/MDRE recognition sequences within a target DNA. Furthermore, this approach is relatively inefficient, which can reduce the reliability of the results. The only CpG sites that are assessed are those within a small number of restriction enzyme recognition sites and status of those sites may not reflect the status of the entire CpG island in which the site reside. Incomplete digestion leads to frequent false positives, especially when cleavage reactions are subjected to a subsequent amplification step. Restriction endonuclease cleavage assays have poor sensitivity compared to bisulfite methods, such as MSP, allowing detection of not less than 10% methylated DNA in a sample (Singer-Sam et al. Nucleic Acids Res, 1990. 18:687; Yegnasubramanian et al. Nucleic Acids Res. (2006) 34:e19).

Chromatin Immunoprecitipation Methods. A third method that is commonly employed for detecting mCpG is chromatin immunoprecipitation (ChIP). Typically, cells are fixed, and then methylated DNA is immunoprecipitated by the use of antibodies specific for methyl binding proteins. The resulting DNA is amplified, labeled and analyzed by hybridization in a microarray assay. The advantages of this method are that the assay can be performed from live cells with little or no DNA purification required. The assay also has increased sensitivity, as unwanted and contaminant DNA are removed prior to analysis. However, the ChIP procedure is very time-consuming, involves several steps and requires expensive reagents. Some assays may take as long as five days to complete.

Methods using Methyl Binding Proteins. An alternative and more sensitive approach to separating methylated from unmethylated DNAs involves the use of methyl-CpG binding domain (MBD) proteins or antibodies against 5-methyl-C. MBD proteins have high affinity for methylated CpG sites and very low affinity for unmethylated DNA (Fraga et al. Nucleic Acids Res. (2003) 31:1765-74). Samples are incubated with immobilized MBD protein in a variety of formats (magnetic beads, columns, the walls of PCR tubes). Methylated DNA capture is usually followed by amplification of the captured DNA. MBD-based DNA detection has the major advantage that all of the methylated sites can contribute to binding, thereby allowing an entire island to be sampled for methyl-CpGs. This characteristic makes the binding assay less vulnerable to false negatives that affect MSP and restriction endonuclease-based assays when unmethylated sites in a partially methylated island correspond to priming/probe sites (Yegnasubramanian et al. Nucleic Acids Res. (2006) 34:e19). This situation is likely to be common in clinical samples containing early stage tumor cells that contain partially methylated CpG islands. MBD based binding assays are very sensitive, allowing detection of as little as 160 pg of methylated DNA (equivalent to ~25 cells) or 1 methylated molecule in 500 unmethylated molecules (Gebhard et al. Nucleic Acids Res. (2006) 34:e8256). This is close to the sensitivity of MSP (1 methylated molecule/1,000 unmethylated molecules). The COMPARE MBD assay can be as sensitive as real-time MSP (1 methylated molecule/10,000 unmethylated molecules) by including digestion with HpaII (an MSRE) before the binding step. Cleavage of unmethylated DNAs at a location between PCR priming sites gives high sensitivity with DNA mixtures that contain artificially methylated DNAs that are fully methylated (Yegnasubramanian et al. Nucleic Acids Res. (2006) 34:e19). However this strategy could suffer the disadvantage associated with the use of restriction endonucleases in that some partially methylated islands will be scored as unmethylated in clinical samples (Yegnasubramanian, et al. supra).

Given the importance of CpG methylation in cancer development and progression, a rapid, reliable, and sensitive test for methylated CpG DNA would provide an important and useful tool for cancer screening.

SUMMARY OF THE INVENTION

The present invention provides methods for detecting target polynucleotides in a sample. The methods generally involve contacting a sample containing a target polynucleotide with a primer pair that specifically hybridizes to and amplifies a target sequence of the polynucleotide. For this step, the primer pair includes a first primer with a 3' sequence complementary to a first sequence flanking the target polynucleotide sequence, and a 5' capture tag. The second primer of the pair has a 3' sequence complementary to a second sequence flanking the polynucleotide target sequence on the opposite strand, and a 5' sequence that provides a means for directing Abscription. Following amplification (e.g. PCR) using this primer pair, the amplified target sequence is contacted with an immobilized molecule that binds the 5' capture tag, to capture the amplified target sequence. At least one Abscript is then transcribed from the means for directing Abscription and the Abscript detected as an indication of the presence of the target polynucleotide.

Capture will typically be via an affinity reagent or binding pair bound or capable of being bound to a solid support. For example, the 5' capture tag can be biotin, which can be readily incorporated into oligonucleotide primers, and the molecule that binds to the 5' capture tag can be streptavidin immobilized on a solid support. A wide variety of solid supports are suitable for use in the methods of the present invention, such as beads, tubes, and microtiter plates. Conveniently, steptavidin and other binding pair molecules can be bound to magnetic beads which permit rapid separation of the solid phase from unbound reagents in solution. In certain embodiments of the invention, unbound reagents, primers, and polynucleotides can be washed from immobilized and captured polynucleotides prior to the subsequent steps in the procedure, which may increase the efficiency of the method. However, this is not necessary as the entire method can be performed in a single pot or tube without separation steps.

PCR is typically used for the amplification step, using for example, a thermostable DNA polymerase or a thermostable RNA polymerase. However, a variety of target amplification methods known in the art may be suitable for use in the methods of the present invention A variety of methods are available for detecting Abscripts as described herein, including, but not limited to mass spectrometry, capillary electrophoresis or thin layer chromatography. In certain aspects, a detectably labeled nucleotide or other label can be incorporated into Abscript signals generated by the methods of the invention to increase the sensitivity or expand the detection techniques that may be used. For example, the detectably labeled nucleotide can be a fluorescent nucleotide.

Abscripts generated by the present invention will generally be short, e.g. 3-20 nucleotides in length. Abscripts as small as 3 nucleotides in length are typically used in the methods described herein.

The second primer of the pair used during amplification has a 3' sequence complementary to a second sequence flanking the target sequence of the polynucleotide on the opposite strand, and a 5' sequence that provides a means for directing Abscription.

In certain embodiments, the means is provided by an α-TAP (Target Attachment Probe) sequence that is used to tag or identify the target. The α-TAP is designed to be complementary to a TAP sequence and permits the attachment of an APC (Abortive Promoter Cassette). To maintain the α-TAP as a single-strand that is thereby available for hybridization to the a TAP sequence, a non-natural nucleotide can be included between the 5' α-TAP sequence and the 3' sequence complementary to the sequence flanking the target in the primer. Non-natural nucleotides, such as etheno-deoxyadenosine, are not recognized by polymerases during amplification. Thus, sequences downstream from the non-natural nucleotide in a primer are not replicated and those sequences remain single-stranded.

Once an APC is bound to the amplified target through the TAP-α-TAP hybrid that is formed, Abscripts are transcribed from the APC as an indication or signal for detecting the presence of the target. The APC that is bound is either a double-strand region or is made double stranded by hybridization of a probe.

In certain embodiments of the invention, a fully duplex APC can be generated during the amplification reaction from a primer sequence that includes one strand of the APC. Conveniently, Abscription can be performed during the amplification by including a thermostable RNA polymerase and nucleotides in the reaction. Thus, in these embodiments, the second primer for the amplification reaction includes an APC sequence. As duplex APCs are generated (e.g. by PCR), Abscripts are transcribed from the APC and can be detected as they are produced (e.g. in real-time), or analyzed at a later time by Abscript detection methods described herein.

The invention provides rapid, sensitive, and specific methods for detecting a variety of variety of target polynucleotides of interest, including DNA and RNA targets, with an expanded repertoire of detection techniques as compared to PCR. Unlike PCR, the methods are also suitable for detecting polynucleotide targets that are modified, such as methylated DNA targets. According to such methods, methylated genomic DNA fragments are first isolated by cleaving a genomic DNA sample containing a methylated target polynucleotide (such as a CpG island), with a restriction enzyme that does not cleave the target polynucleotide, or generates suitably representative fragments of the target for during cleavage. The cleaved genomic DNA is then contacted with an immobilized methyl binding domain, such as the GST-MBD2 fusion protein described herein. In this way, methylated genomic DNA fragments are immobilized and therefore isolated from the non-methylated DNA fragments in the sample. Optionally, the methylated genomic DNA fragments can be eluted from the immobilized MBD and recovered prior to analysis. For example, where the GST-MBD2 fusion protein is used for immobilizing methylated CpG island targets, the GST portion of the fusion protein can be bound to a glutathione resin (before or after interaction with DNA), and the bound methylated DNA fragments can be eluted with glutathione.

The methods of the invention are also suitable for multiplexing. According to certain embodiments of the invention, the a plurality of different target polynucleotides, are processed simultaneously by including a plurality of first and second primer pairs in the reactions, each primer pair being designed to specifically hybridize to a different target polynucleotide. By designing different, unique APCs for each target that are attached to the target through the primed amplification (either as part of the APC-containing primer or via the TAP-α-TAP hybrid, as described herein), the presence of each of the plurality of target can be identified through the APC signal that is genereated. For example, each APC can be designed to be distinguishable on the basis of molecular weight or nucleotide sequence. According to these embodiments of the invention, at least 5, 10, 20, 50, 100 or more targets can be detected in a single assay.

BRIEF DESCRIPTION OF THE DRAWINGS

FIG. 2C illustrates an embodiment of the invention where the APC is attached to an antibody. The target protein can be "sandwiched" between an APC-antibody complex and a second antibody immobilized on a solid support, for capture and detection of the protein targets similar to strategies used in enzyme linked immunosorbent assays (ELISA).

FIG. 4A shows the column profile in terms of total ion count as a function of retention time. FIG. 4B shows the ion spectrum for the trinucleotide Abscript GAG peak (retention time 5.4 min). Singly- and doubly-charged GAG species have m/z values of 956.1 and 477.6, respectively. The sodium adduct of the double charged species has a m/z of 978.2.

FIG. 5 A shows the linkage of a MBD domain to the carboxyl end of a GST domain. The amino acid sequence linking the domains (SEQ ID NO:1) contains a thrombin cleavage site indicated by the arrow. FIG. 5B shows the amino acid sequence for the DNA binding domain of mouse MBD2b (SEQ ID NO:2). The underlined amino acids correspond to conserved residues among the DNA binding domains of MBD proteins (Ohki et al. (1999) EMBO J. 18:6653-61). FIG. 5 C shows the results of methylated DNA fractionation using immobilized GST-MBD. The S (supernatant) fraction contains amplified unmethylated SNRPN CpG island DNA. E1 contains amplified methylated SNRPN CpG island DNA that was eluted from the immobilized protein. Fractions E2 and E3 are two additional serial elutions from the same immobilized protein. FIG. 5 D shows the fractionation of PTGS2 DNA, which is unmethylated, in HeLa cells. All of the PTGS2 DNA is recovered in the unbound supernatant fraction S.

FIG. 6 is a flow diagram illustrating the strategy for α-TAP Abscription®-based CpG methylation detection including the binding of a TAP-APC to an amplified fragment of a target CpG island. Steps in the process are indicated by numerals. FIG. 6A illustrates the initial capture of methylated CpG containing DNA. Step 1: Methylated DNA fragments are separated from unmethylated DNA fragments with an immobilized GST-MBD protein. Step 2: Methylated DNA fragments are released by heat treatment or exposure to protease or glutathione. FIG. 6B shows amplification tagging and capture of tagged DNA fragments. Step 3: A target CpG island is tagged with an affinity label such (as biotin (B), as shown) and a single-strand extension during PCR, through the incorporation of a biotinylated primer and a primer containing a non-coding nucleotide between the primer sequence and an anti-TAP sequence (α-TAP). Step 4: The biotinylated amplicon is bound to streptavidin-magnetic beads. Step 5: The APC is bound to the amplicon by hybridization between the TAP sequence and the α-TAP sequence. Abscription® is performed by contacting an RNA polymerase (RNAP) with the bead-immobilized complexes containing APCs.

FIGS. 7A-7C illustrate the interactions between exemplary target-specific amplification primers and anti-TAP (α-TAP) primer/probes. FIG. 7A illustrates the PCR primers used in CpG island amplification and their relative locations in the amplicon. FIGS. 7B and 7C illustrate unfavorable assay outcomes by poorly designed α-TAP primer/probes.

FIG. 8A shows the TaqMan® PCR results. TaqMan® PCR primers were SEQ ID NO: 3 and SEQ ID NO: 4. Detection of 9000 copies required 28 PCR cycles. FIG. 8 B shows the results of the Abscription®/PCR detection following 29 PCR cycles. Abscription/PCR primers were SEQ ID NO:12 and SEQ ID NO:13. The TAP-APC was made by annealing SEQ ID NO:28 and SEQ ID NO:32. The APC encoded the Abscript GAG. Abscripts were detected using thin layer chromatography (TLC) and UV shadowing. Area refers to the area of the chromatographic peak containing the Abscript.

FIG. 10 is a flow diagram showing the strategy for methylated DNA detection using direct incorporation of an APC into amplicons with the use of an APC-primer. Numerals indicate steps in the strategy. Steps 1 and 2 depict the fractionation of methylated DNA using immobilized GST-MBD protein, as illustrated in FIG. 6A. Step 3 shows the relationship between the targeted sequence and the primers that are used to attach an APC to the amplicon. The leftward primer is a conventional PCR primer. The rightward primer has a 3' priming sequence and a single-stranded APC at the 5' end. Steps 4 and 5 represent PCR amplification of the target. Step 6 represents the Abscription® step following PCR. The PCR reaction is supplemented with RNA polymerase, initiator and one or more NTPs.

FIG. 11 illustrates the validation of an APC promoter pair for the GAPDH CpG island. FIG. 11 A shows the evaluation of background signal due to self-priming by the APC primer C443 and background due to the formation of primer-dimers between C443 (SEQ ID NO:33) and the reverse primer C446 (SEQ ID NO:34). PCR reactions lacking DNA containing C443 alone or a combination of C443 and C446 were performed at a range of annealing temperatures from 56.4° C. to 68.5° C. followed by 1 hr of Abscription®. The production of Abscripts was assayed by TLC-UV shadowing. Only the positive control containing HeLa DNA produced the Abscript GAG. FIG. 11 B shows the results of LC-MS detection of Abscripts from the same sample sets.

DETAILED DESCRIPTION

Definitions

Figure 1:
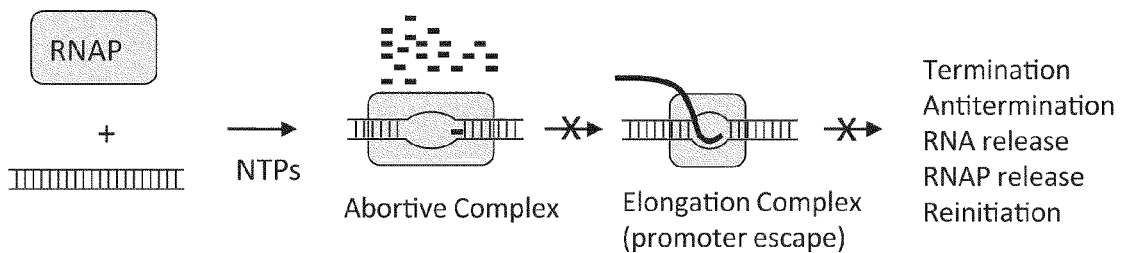
FIG. 1 illustrates the process of abortive transcription, which is exploited by the Abscription® methods of the invention. Abortive transcription occurs on most promoters when RNA polymerase (RNAP) is trapped at the promoter repeatedly making short abortive transcripts (typically 2 to 12 nt long). During abortive transcription, the RNAP does not translocate or leave the promoter. During normal transcription, RNAP eventually undergoes a conformational change to a stable, processive elongation complex, a process called promoter escape, and then continues transcription until a termination signal is reached. Artificial promoters, or Abortive Promoter Cassettes (APCs) have been developed that trap RNAP in an abortive complex, reiteratively synthesizing thousands of identical short oligonucleotides per minute. Each APC is designed to make a different Abscript of specific length and sequence which can be separated and quantified.

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. As used herein, the terms "comprises," "comprising", "includes", and "including", or any other variations thereof, are intended to cover a non-exclusive inclusion, such that a process, method, composition, reaction mixture, kit, or apparatus that comprises a list of elements does not include only those elements but may include other elements not expressly listed or inherent to such process, method, composition, reaction mixture, kit, or apparatus. The section headings used herein are for organizational purposes only and are not to be construed as limiting the subject matter described.

Unless specific definitions are provided, the nomenclatures utilized in connection with, and the laboratory procedures and techniques of molecular biology, biochemistry, and organic chemistry described herein are those known in the art. Standard chemical and biological symbols and abbreviations are used interchangeably with the full names represented by such symbols and abbreviations. Thus, for example, the terms "deoxyribonucleic acid" and "DNA" are understood to have identical meaning Standard techniques may be used e.g., for chemical syntheses, chemical analyses, recombinant DNA methodology, and oligonucleotide synthesis. Reactions and purification techniques may be performed e.g., using kits according to manufacturer's specifications, as commonly accomplished in the art or as described herein. The foregoing techniques and procedures may be generally performed according to conventional methods well known in the art and as described in various general or more specific references that are cited and discussed throughout the present specification. See e.g., Sambrook et al. *Molecular Cloning: A Laboratory Manual* (2d ed., Cold Spring Harbor Laboratory Press, Cold Spring Harbor, N.Y. (1989)); Ausubel et al. *Current Protocols in Molecular Biology* (John Wiley & Sons Inc., N.Y. (2003)), the contents of which are incorporated by reference herein in their entirety for any purpose.

"About" as used herein means that a number referred to as "about" comprises the recited number plus or minus 1-10% of that recited number. For example, "about" 50 nucleotides can mean 45-55 nucleotides or as few as 49-51 nucleotides depending on the situation. Whenever it appears herein, a numerical range, such as "45-55", refers to each integer in the given range; e.g., "45-55 nucleotides" means that the nucleic acid can contain 45 nucleotides, 46 nucleotides, etc., up to and including 55 nucleotides.

"Transcription" as used herein, refers to the enzymatic synthesis of an RNA copy of one strand of DNA (i.e, template) catalyzed by an RNA polymerase (e.g. a DNA-dependent RNA polymerase).

"Abortive transcription" is an RNA polymerase-mediated process that reiteratively synthesizes and terminates the synthesis of oligonucleotides that correspond to at least one portion of a complementary nucleic acid template sequence. Abortive oligonucleotides synthesized in vivo vary in length of nucleotides, and are complementary to a sequence at or near the transcription initiation site.

"Abscription®" is a form of abortive transcription optimized for in vitro analytical use to reiteratively produce short, uniform RNA transcripts or "abscripts" from synthetic or naturally occurring promoter sequences at high frequency in vitro. The term "Abscripts" (capitalized), is used herein to distinguish optimized, synthetic transcripts produced in an Abscription® reaction or assay, from the more general term "abscripts," which also encompasses short abortive transcripts that are produced during the normal course of transcription as it occurs in nature.

"Reiterative" refers to the repetitive synthesis of multiple identical or substantially identical copies of a sequence of interest.

"Terminator" or "transcription terminator" as used herein, refers to an RNA chain terminating compound, complex or process. A terminator of the invention can, for example, be a nucleotide analog, which can be incorporated into an RNA chain during RNA synthesis to prevent the addition of additional nucleotides to the RNA chain.

"Amplification" as used herein, refers to the process of making identical copies of a polynucleotide, such as a DNA fragment or region. Amplification is generally accomplished by polymerase chain reaction (PCR), but other methods known in the art may be suitable to amplify DNA fragments of the invention.

A "target DNA sequence" or "target DNA" is a DNA sequence of interest for which detection, characterization or quantification is desired. The actual nucleotide sequence of the target DNA may be known or not known. Target DNAs are typically DNAs for which the CpG methylation status is interrogated. A "target DNA fragment" is a segment of DNA containing the target DNA sequence. Target DNA fragments can be produced by any method including e.g., shearing or sonication, but most typically are generated by digestion with one or more restriction endonucleases.

As used herein, a "template" is a polynucleotide from which a complementary oligo- or polynucleotide copy is synthesized.

"Synthesis" generally refers to the process of producing a nucleic acid, via chemical or enzymatic means. Chemical synthesis is typically used for producing single strands of a nucleic acid that can be used as primers and probes. Enzyme mediated "synthesis" encompasses both transcription and replication from a template. Synthesis includes making a single copy or multiple copies of the target. "Multiple copies" means at least 2 copies. A "copy" does not necessarily mean perfect sequence complementarity or identity with the template sequence. For example, copies can include nucleotide analogs, intentional sequence alterations (such as sequence alterations introduced through a primer comprising a sequence that is hybridizable, but not complementary, to the template), and/or sequence errors that occur during synthesis.

The terms "polynucleotide" and "nucleic acid (molecule)" are used interchangeably to refer to polymeric forms of nucleotides of any length. The polynucleotides may contain deoxyribonucleotides, ribonucleotides and/or their analogs. Nucleotides may be modified or unmodified and have any three-dimensional structure, and may perform any function, known or unknown. The term "polynucleotide" includes single-stranded, double-stranded and triple helical molecules. The following are non-limiting embodiments of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers.

"Oligonucleotide" refers to polynucleotides of between 2 and about 100 nucleotides of single- or double-stranded nucleic acid, typically DNA. Oligonucleotides are also known as oligomers or oligos and may be isolated from genes and other biological materials or chemically synthesized by methods known in the art. A "primer" refers to an oligonucleotide containing at least 6 nucleotides, usually single-stranded, that provides a 3'-hydroxyl end for the initiation of enzyme-mediated nucleic acid synthesis. A "polynucleotide probe" or "probe" is a polynucleotide that specifically hybridizes to a complementary polynucleotide sequence. As used herein, "specifically binds" or "specifically hybridizes" refers to the binding, duplexing, or hybridizing of a molecule to another molecule under the given conditions. Thus, a probe or primer "specifically hybridizes" only to its intended target polynucleotide under the given binding conditions, and an antibody "specifically binds" only to its intended target antigen under the given binding conditions. The given conditions are those indicated for binding or hybridization, and include buffer, ionic strength, temperature and other factors that are well within the knowledge of the skilled artisan. The skilled artisan will also be knowledgeable about conditions under which specific binding can be disrupted or dissociated, thus eluting or melting e.g, antibody-antigen, receptor-ligand and primer-target polynucleotide combinations.

"Nucleic acid sequence" refers to the sequence of nucleotide bases in an oligonucleotide or polynucleotide, such as DNA or RNA. For double-strand molecules, a single-strand may be used to represent both strands, the complementary stand being inferred by Watson-Crick base pairing.

The terms "complementary" or "complementarity" are used in reference to a first polynucleotide (which may be an oligonucleotide) which is in "antiparallel association" with a second polynucleotide (which also may be an oligonucleotide). As used herein, the term "antiparallel association" refers to the alignment of two polynucleotides such that individual nucleotides or bases of the two associated polynucleotides are paired substantially in accordance with Watson-Crick base-pairing rules. Complementarity may be "partial," in which only some of the polynucleotides' bases are matched according to the base pairing rules. Or, there may be "complete" or "total" complementarity between the polynucleotides. Those skilled in the art of nucleic acid technology can determine duplex stability empirically by considering a number of variables, including, for example, the length of the first polynucleotide, which may be an oligonucleotide, the base composition and sequence of the first polynucleotide, and the ionic strength and incidence of mismatched base pairs.

As used herein, the term "hybridization" is used in reference to the base-pairing of complementary nucleic acids, including polynucleotides and oligonucleotides containing 6 or more nucleotides. Hybridization and the strength of hybridization (i.e., the strength of the association between the nucleic acids) is impacted by such factors as the degree of complementarity between the nucleic acids, the stringency of the reaction conditions involved, the melting temperature ($T_m$) of the formed hybrid, and the G:C ratio within the duplex nucleic acid. Generally, "hybridization" methods involve annealing a complementary polynucleotide to a target nucleic acid (i.e., the sequence to be detected either by direct or indirect means). The ability of two polynucleotides and/or oligonucleotides containing complementary sequences to locate each other and anneal to one another through base pairing interactions is a well-recognized phenomenon.

A "complex" is an assembly of components. A complex may or may not be stable and may be directly or indirectly detected. For example, as described herein, given certain components of a reaction and the type of product(s) of the reaction, the existence of a complex can be inferred. For example, in the abortive transcription method described herein, a complex is generally an intermediate with respect to a final reiterative synthesis product, such as a final abortive transcription or replication product.

"Methylation" refers to the addition of a methyl group ($-CH_3$) to a molecule, typically to a nucleotide base in DNA or RNA. "mCpG" refers to a 5'-CG-3' dinucleotide in which the C is methylated at position 5 (5-methylcytosine or 5-Me C). "CpG islands" are regions of genomic DNA that contain a high frequency of the CpG dinucleotide. CpG Islands are in or near approximately 40% of promoters of mammalian genes and about 70% of human promoters have a high CpG content. See e.g. Fatemi et al. (2005) Nucleic Acids Res. 33:e176. doi:10.1093/nar/gni180. PMID 16314307.

"Promoter" as used herein, refers to a region of DNA that facilitates the transcription of an adjacent gene. Promoters are typically 5' and proximal to the start site of transcription initiation in a gene, and direct an RNA polymerase and associated transcription factors to the correct location for transcription of a the gene.

"Microarray" and "array," are used interchangeably to refer to an arrangement of a collection of compounds, samples, or molecules such as oligo- or polynucleotides. Arrays are typically "addressable" such that individual members of the collection have a unique, identifiable position within the arrangement. Arrays can be formed on a solid substrate, such as a glass slide, or on a semi-solid substrate, such as nitrocellulose membrane, or in vessels, such as tubes or microtiter plate wells. A typical arrangement for an array is an 8 row by 12 column configuration, such as with a microtiter plate, however, other arrangements suitable for use in the methods of the present invention will be well within the knowledge of the skilled artisan.

The term "solid support" refers to any solid phase that can be used to immobilize e.g., a capture probe or other oligo- or polynucleotide, a polypeptide, an antibody or other desired molecule or complex. Suitable solid supports will be well known in the art and include, but are not limited to, the walls of wells of a reaction tray, such as a microtiter plate, the walls of test tubes, polystyrene beads, paramagnetic or non-magnetic beads, glass slides, nitrocellulose membranes, nylon membranes, and microparticles such as latex particles. Typical materials for solid supports include, but are not limited to, polyvinyl chloride (PVC), polystytrene, cellulose, agarose, dextran, glass, nylon, latex and derivatives thereof. Further, the solid support may be coated, derivatized or otherwise modified to promote adhesion of the desired molecules and/or to deter non-specific binding or other undesired interactions. The choice of a specific "solid phase" is usually not critical and can be selected by one skilled in the art depending on the methods and assays employed. Conveniently, the solid support can be selected to accommodate various detection methods. For example, 96 or 384 well plates can be used for assays that will be automated, for example by robotic workstations, and/or those that will be detected using, for example, a plate reader. For methods of the present invention that may involve e.g. an autoradiographic detection step utilizing a film-based visualization, the solid support may be a thin membrane, such as a nitrocellulose or nylon membrane, a gel or a thin layer chromatography plate. Suitable methods for immobilizing molecules on solid phases include ionic, hydrophobic, covalent interactions and the like, and combinations thereof. However, the method of immobilization is not typically important, and may involve uncharacterized adsorbtion mechanisms. A "solid support" as used herein, may thus refer to any material which is insoluble, or can be made insoluble by a subsequent reaction. The solid support can be chosen for its intrinsic ability to attract and immobilize a capture reagent. Alternatively, the solid support can retain additional molecules which have the ability to attract and immobilize e.g., a "capture" reagent.

"Antibody" or "antibodies", as used herein, include naturally occurring species such as polyclonal and monoclonal antibodies as well as any antigen-binding portion, fragment or subunit of a naturally occurring molecule, such as for example Fab, Fab', and F(ab)$_2$ fragments of an antibody. Also contemplated for use in the methods of the invention are recombinant, truncated, single chain, chimeric, and hybrid antibodies, including, but not limited to, humanized and primatized antibodies, and other non-naturally occurring antibody forms.

The present invention is based on a molecular detection technology called Abscription® which is in turn based on the natural phenomenon known as abortive transcription (FIG. 1). Abscription® is a robust, isothermal method for detecting and quantifying a wide range of targets including proteins, nucleic acids, SNPs and CpG methylation (U.S. patent application Ser. Nos. 10/602,045, 10/790,766, and 10/488,971; U.S. Pat. Nos. 7,045,319, and 7,226,738). Abscription® occurs during the initiation phase of transcription in which RNA polymerase (RNAP) reiteratively generates short RNAs, or aborted transcripts (Abscripts), while remaining tightly bound to the promoter (Hsu, Biochim. Biophys. Acta (2002) 1577:191-207; Hsu et al. Biochemistry (2003) 42:3777-86; Vo et al. Biochemistry (2003) 42:3798-811; Vo et al. Biochemistry (2003) 42:3787-97; Hsu et al. Biochemistry (2006) 45:8841-54). The sequences of the promoter and the initially transcribed segment have significant effects on the lengths of the predominant Abscripts, as well as their rates of synthesis (Hsu et al. Biochemistry (2006) 45:8841-54.28).

Multiple optimal highly abortive promoters, called Abortive Promoter Cassettes (APCs), have been developed and optimized to make Abscripts of different sequences and lengths (between 3 and 12 nt) at extremely high rates.

The generation of short Abscripts is very efficient because the RNAP does not dissociate from the promoter between rounds of truncated RNA synthesis, as it does after producing each full length transcript, and will continue to produce Abscripts at high turnover rates until substrates are depleted. This results in the very rapid production of thousands of Abscripts per APC each minute. Abscription® is a signal amplification, rather than a target amplification process.

The present invention provides simple and sensitive methods for the detection of CpG methylation in DNA via mCpG target site probes that include optimized methyl binding domain (MBD) polypeptides. mCpG target site probes can be coupled directly or indirectly to a signal generator, which produces a detectable signal that can be measured as an indicator of CpG methylation.

In certain embodiments of the invention, signal generation is based on an Abscription® process in which Abortive Promoter Cassettes (APCs) signal generators are bound to target mCpG sites via mCpG target specific probes. RNA polymerase produces uniform, short RNA molecules from synthetic or naturally occurring abortive promoters in APCs as signals (indicators) of the presence of methylated CpGs. In other embodiments of the invention, signal-generating cassettes can produce detectable RNA or DNA signals through PCR or other replication and/or amplification methods.

The methods of the invention offer significant advantages over current CpG methylation detection methods because bisulfite treatment is not required. Thus, the extensive DNA degradation and the reduction of sequence complexity associated with chemical treatment of target DNA can be avoided entirely in certain embodiments of the invention. The methods of the invention are rapid and can typically be performed in a single day. Furthermore, the invention can be adapted to multiplex and automated applications.

Certain Abscription®-based methylation detection assays of the present invention offer the unique capability of coupling a linear, robust signal amplification process (Abscription®) with a target amplification process (e.g. polymerase chain reaction or PCR). This provides for extremely high sensitivity and allows testing to use only small amounts of starting material. In addition, unlike other signal amplification methods, such as horseradish peroxidase or alkaline phosphatase, which generate the same signal molecule from each target in a sample, Abscription® based amplification can be formatted to generate a different signal from each target. These signals, in the form of short oligonucleotides, can then be detected by a variety of methods. Abscription®-based assays require fewer man-hours of labor than other DNA methylation detection assays, reagent cost is very competitive, and instrumentation cost is low. In addition, these assays, by including positive and negative control templates, result in highly specific detection and fewer false positives than other methods for target detection.

Abscription® Technology

Abscription® technology is based on the observation that prior to the initiation of full-length RNA transcription, a large number of short, abortive transcripts are synthesized by RNA polymerases before full-length RNA transcripts are made. As described below, abortive transcripts are a normal by-product of the transcription process, yet are distinguishable from full-length RNA transcripts (which are the functionally informative product of the transcription process), in both size and in the manner in which they are made.

Transcription Process. Transcription is a complex and highly regulated process utilized by both eukaryotes and prokaryotes to selectively synthesize RNA transcripts from DNA templates (i.e. genes) (reviewed in Record et al. (1996) *Escherichia coli* and *Salmonella*, (Neidhart, ed.; ASM Press, Washington, D.C.); deHaseth et al. (1998) J. Bact. 180:3019-25; Hsu (2002) Biochim. Biophys. Acta. 1577:191-207; Murakami & Darst (2003) Curr. Opin. Struct. Biol. 13:31-39; Young et al. (2002). Cell. 109:417-420). Transcription in a cellular environment includes 5 stages: 1. Preinitiation, during which transcriptional machinery (e.g. RNA polymerase (RNAP) and transcription factors), is recruited to a promoter; 2. Initiation, during which synthesis of RNA begins; 3. Promoter Escape, during which the RNA polymerase leaves the promoter and abortive initiation stops (usually after synthesis of approximately 12-mer RNAs); 4. Elongation, during which RNAP travels processively along the template DNA strand, thereby synthesizing a full-length RNA transcript; and 5. Termination, during which RNA synthesis ceases and RNAP dissociates from the template DNA.

Production of Abortive Transcripts Prior to Full-Length RNA Transcription. Typically, RNAP fails to escape from the promoter on its first attempt and, instead, engages in multiple abortive cycles of synthesis and release of short RNA products called abortive transcripts. Only when RNAP succeeds in synthesizing an RNA product of a threshold length does RNAP irrevocably break its interactions with promoter DNA, and begin to translocate along the DNA template, processively synthesizing a full-length RNA transcript (see Hsu (2002) Biochim. Biophys. Acta. 1577:191-207; Hsu et al. (2003) Biochemistry 42: 3777-86; Vo et al. (2003) Biochemistry 42:3787-97; Vo et al. (2003) Biochemistry: 42:3798-11). Prior to promoter escape in (stage 3, above), RNAP remains bound to template DNA at or near the promoter region, thereby allowing multiple rounds of abortive synthesis in a short time.

Abscription® Technology. Abscription® technology exploits the natural phenomenon of abortive RNA synthesis to produce large numbers of detectable abortive transcripts (Abscripts). Abscription® is an isothermal, robust, linear signal generation system based on abortive transcription. In an Abscription® method, Abortive Promoter Cassettes (APCs) are bound to target molecules via Target Site Probes (TSPs). An RNA polymerase, such as *E. coli* RNA polymerase, then uses the APC as a template for generating large numbers of signals per target in the form of short, uniform RNA molecules or Abscripts (abortive transcripts).

Abscription® detection methods have three basic steps that can be adapted to detect a wide variety of molecules of interest (i.e. targets). First, an APC is localized to a target molecule of interest through a Target Site Probe (TSP). Second, Abscripts are synthesized from the localized APCs. Finally, Abscripts are detected as a means of target detection and may be quantified as an indication of the amount of a target molecule present. The process is very efficient because the RNAP does not move away or dissociate from the promoter between rounds of abortive RNA synthesis, as it does after producing each full-length transcript. Furthermore, only uniform, short RNA signals are synthesized, which can be produced more quickly and with less effort than longer oligo- and polynucleotides.

Figure 3:
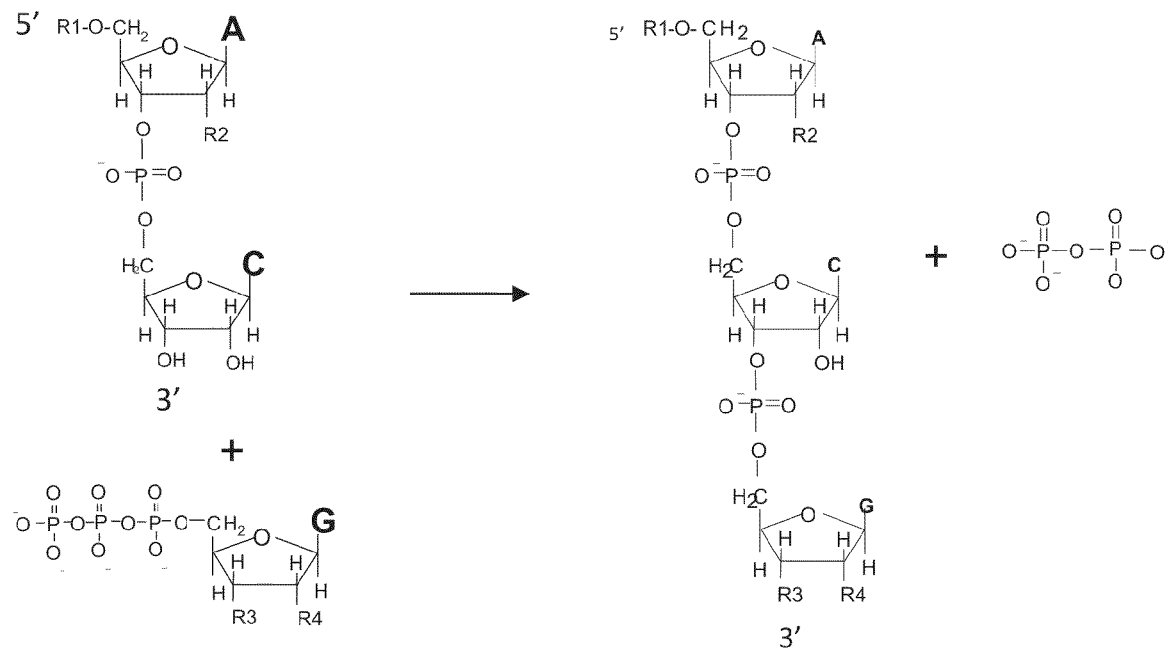
FIG. 3 illustrates dinucleotide initiation of Abscription® and termination after the addition of one NTP. Abscript length can be limited by inclusion of chain terminating NTPs (3'-O-Me-NTPs at R3) as depicted, or by omitting one or more NTPs from the reaction. R1=Affinity tag, Fluorescent Tag; R2=OH, OMe, H; R3=OH, OMe, H; R4=OH, OMe, H.

Although the factors and conditions required for promoter escape (and hence the end of abortive synthesis), are incompletely understood, sufficient knowledge is available to create a synthetic environment that favors abortive transcript synthesis and precludes full-length RNA production. In one embodiment, Abscription® is controlled at the synthesis stage to produce Abscripts that are initiated with a defined dinucleotide initiator and then terminated after the addition of one or more NTPs as illustrated in the nonlimiting example shown in FIG. 3. Abscript length can be limited to as short as 3 nucleotides (nt) with the use of chain terminating NTPs (e.g., 3'-O-Me-NTPs) or by omitting one or more NTPs from the reaction.

In other embodiments, Abscript length is controlled at the promoter/template stage, by providing synthetic templates that have a discrete, limited number of nucleotides available for transcription before a stop signal is reached. The uniformity of Abscript production from a single APC in a single Abscription® reaction results in Abscript signals that are directly proportional to the amount of target present. Thus Abscription® is both a qualitative and a quantitative system for measuring a target, such as mCpG.

Figure 2:
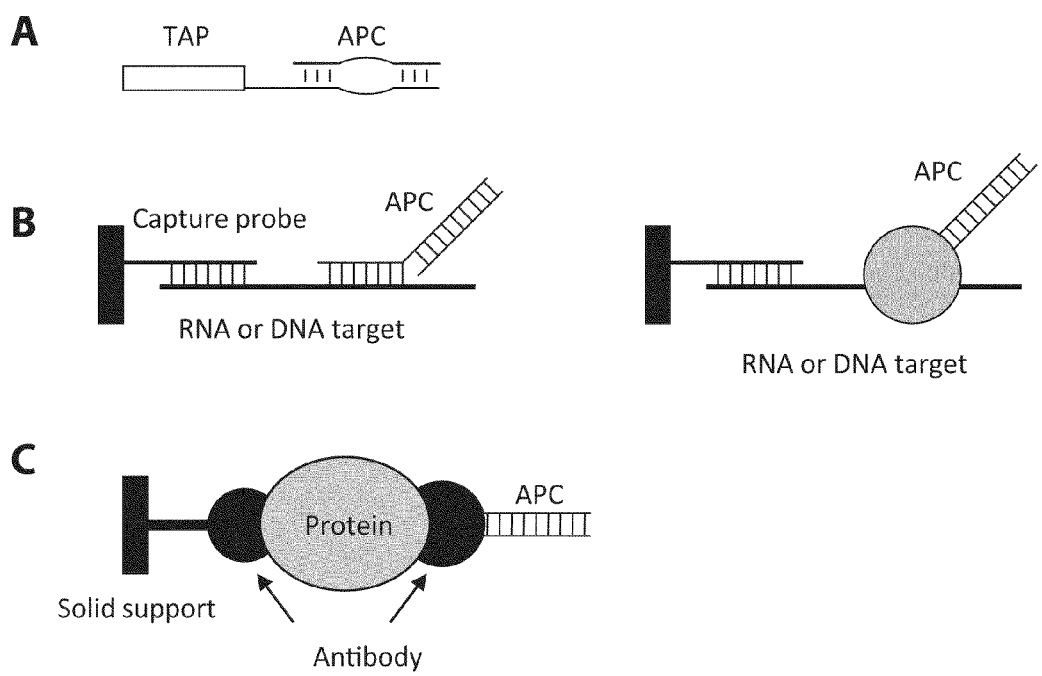
FIG. 2 illustrates detection of protein, RNA and DNA targets using Abscription®. APCs are attached to a Target Attachment Probe (TAP), which specifically binds to the molecular target (FIG. 2A). For detection of DNA and RNA, TAPs include oligonucleotides that specifically hybridize to or proteins that bind specifically to the nucleic acid target (FIG. 2B). For protein detection, APCs can be attached to any molecule that binds to the protein target, such as an antibody or a ligand.

Abortive promoters can be incorporated into DNA targets through a target amplification processes or formed on single-stranded DNA targets by hybridization of a second strand. More generally however, Abscription® can be used to detect a wide variety of target molecules by binding APCs to those targets (FIG. 2). For detection of protein, RNA or DNA, APCs are connected to a Target Attachment Probe (TAP) which will bind to the molecular target (FIG. 2A). For detection of DNA and RNA, TAPs include oligonucleotides or proteins that bind specifically to the nucleic acid target (FIG. 2B). For protein detection, APCs can be attached to anything that binds to the protein target. Several assays have been developed which employ two antibodies directed to the same target, similar to ELISA, one for capture of the target and one for attachment of the APC (FIG. 2C).

Trinucleotide Synthesis

Trinucleotide Abscripts can be made exclusively with the inclusion of chain terminator NTPs or by omitting one or more NTP. Abscripts can be labeled for detection or capture by incorporating modified dinucleotides (Dissinger & Hanna, J. Biol. Chem. (1990) 265:7662-8: Dissinger & Hanna, J. Mol. Biol. (1991) 219:11-25; Hanna, Meth. Enzymol., (1989) 180:383-409; Hanna et al. Biochemistry (1989) 28:5814-20; Hanna & Meares, Proc. Natl. Acad. Sci. USA, (1983) 80:4238-42; Hanna & Meares, Biochemistry (1983) 22:3546-51.29-34), or NTPs (Hanna, et al. Nucleic Acids Res. (1999) 27:1369-76; He et al, Nucleic Acids Res (1995) 23:1231-8) during Abscription®. "Label" as used herein refers to a moiety, the presence of which on a molecule, can be detected and distinguished either directly or indirectly. Labels typically are more readily detected, with higher efficiently and/or specificity than detecting a native, unlabeled species. Label suitable for use in the methods of the present invention include fluorescent groups, affinity tags (such as biotin), and charge or mass modified nucleotides.

In one embodiment, the assays described herein involve the production of different trinucleotide Abscripts that differ by molecular weight or mobility. Trinucleotides are made by RNAP at rates of 1000 to 2000 per minute on APCs by joining a dinucleotide initiator and a nucleoside triphosphate. Trinucleotide Abscripts can be detected without labeling by rapid TLC and UV shadowing or mass spectrometry. Alternatively, Abscripts can be detected through a label (e.g. a fluorescent moiety) incorporated into a dinucleotide initiator.

The present invention provides methods for detecting a polynucleotide in a sample by contacting a sample containing the polynucleotide with a primer pair that specifically hybridizes to and amplifies a target sequence of the polynucleotide. The primer pair includes a first primer that is complementary to the polynucleotide, flanks the target sequence, and contains a 5' capture tag.

The second primer has three regions: a 3' sequence complementary to the polynucleotide that flanks the target sequence on the opposite side of the target sequence from the first primer; a 5' α-TAP sequence that is used to attach the APC following amplification; and a non-natural nucleotide between the 3' and 5' sequences, that is typically an etheno-deoxyadenosine.

The target sequence of the polynucleotide is then amplified (e.g. by polymerase chain reaction) using the first and second primers and the amplified target sequence is captured on a solid support containing a molecule that binds the 5' capture tag. Any available PCR technique or suitable nucleic acid amplification method can be employed for this step, such as PCR methods that use thermostable DNA polymerase and/or RNA polymerase enzymes. For example the capture tag can be biotin and the solid support can be streptavidin beads, such as magnetic beads. The captured amplicons can then be washed to remove unbound primers and, if desired, eluted from the solid support.

For detection of the target polynucleotide sequence, a probe is hybridized to the amplicon. This probe includes a 5' TAP sequence complementary to the α-TAP sequence. Due to the inclusion of the non-natural nucleotide in the second PCR primer, the α-TAP sequence is not copied during PCR and remains single-stranded during the amplification, thereby allowing the TAP sequence of the probe to hybridize without denaturing the amplified target. Etheno-deoxyadenosine can be used as the non-natural nucleotide, but the skilled artisan will be aware of additional suitable non-natural nucleotides (e.g. nucleotide analogs) that terminate replication and can thus be substituted for etheno-deoxyadenosine. The probe also includes an APC, which provides the template for synthesizing Abscripts using Abscription® methods as described above. Finally, the Abscripts are detected by any suitable method, particularly the methods described herein for Abscript detection, such as mass spectrometry, capillary electrophoresis or thin layer chromatography. Typically, the Abscripts will have a length of from 3 to 20 nucleotides and may be labeled by incorporating a detectably-labeled (e.g. fluorescent) nucleotide during Abscription®.

In other embodiments of the invention, the TAP/α-TAP step can be eliminated by including an APC sequence at the 5' end of the second amplification primer and omitting the non-naturally occurring nucleotide. In such embodiments, a double-strand APC is generated during amplification adjacent to the amplified target sequence, which will direct Abscription® upon addition of RNAP and nucleotides. If these Abscription® reagents are present during amplification, Abscription® and amplification can be performed simultaneously in the same tube.

These methods of the invention can be adapted for multiplexing (i.e., detection of a plurality of polynucleotides simultaneously) by including primer pairs specific to each polynucleotide in the reaction. According to this embodiment of the invention, each primer pair is designed to specifically hybridize to and amplify a unique target sequence of a polynucleotide. The α-TAP sequence for each primer pair is also unique, thereby acting as an identifier for the target sequence. By hybridizing a complementary TAP sequence that includes a unique identifying APC following PCR amplification, the presence of each polynucleotide can be interrogated based on the Abscripts produced in the multiplex reaction. Thus a unique APC is attached to each amplified target polynucleotide and the distinguishable Abscript signal produced from the APC can be detected and measured as an indication of the presence of the target polynucleotide. For example, each APC can be designed to generate an Abscript distinguishable on the basis of molecule weight or nucleotide sequence. In a single reaction, 5, 10, 20 or more unique target sequences can be detected.

The present invention also provides methods for determining the methylation status of CpG islands without the use of deamination with bisulfite. Such method combines target amplification with a linear signal amplification process, Abscription®, making it extremely sensitive.

In certain embodiments of the invention, the target polynucleotide(s) is a methylated CpG island or a plurality of CpG islands (i.e. multiplexing). In these embodiments, genomic DNA containing methylated CpG islands is first cleaved using a predetermined restriction enzyme that does not cut the island or any of the islands in a multiplex assay. Methylated DNA fragments are then captured from the genomic DNA using an immobilized MBD reagent and the captured fragments interrogated for specific CpG sequences of interest. According to one method of the invention, the process begins by isolation of methylated DNA from fragmented genomic DNA using a methylated DNA enrichment process. In one aspect of the invention, the enrichment method uses a glutathione-S-transferase fusion protein which contains the methyl binding domain from mouse MBD2, which is highly specific for methylated DNA. Methylated DNA bound to MBD2-fusion protein is captured rapidly by glutathione magnetic beads and eluted directly into buffer for amplification by the polymerase chain reaction. CpG islands of interest are amplified using a pair of modified PCR primers. The first contains a biotin group for subsequent capture of the targeted CpG island to streptavidin magnetic beads. The second primer contains an island-specific sequence that "marks" the amplicon for attachment of a specific APC. Once amplified, islands are captured to streptavidin beads; unique APCs are attached by hybridization; and Abscription® is initiated. Each CpG island thereby generates a different Abscript; therefore multiple CpG islands can be interrogated in each reaction.

Alternatively, an APC sequence can be incorporated into the second amplification primer, and an APC duplex generated during amplification. This approach allows amplification and Abscription® to be performed at the same time by including RNAP and nucleotides in the amplification reaction. Because this method couples target amplification with signal amplification, less starting DNA is required than with most methylated DNA detection methods, and less than 2 ng of genomic DNA is sufficient for the initial step of isolating methylated DNA. The entire assay is very rapid, requiring less operator time than most competing assays. The assay can be used as described with magnetic beads and can also be formatted for high throughput screening in a microtiter plate format.

EXAMPLES

Example 1

Abscription® Methods

Abscription® has been previously described; see e.g. U.S. patent application Ser. No. 09/984,664 (filed Oct. 30, 2001) now U.S. Pat. No. 7,045,319; Ser. No. 10/425,037 (filed Apr. 29, 2003), U.S. Pat. Pub. No. 2004-0054162; Ser. No. 10/600, 581 (filed Jun. 23, 2003) now U.S. Pat. No. 7,541,165; Ser. No. 10/602,045 (filed Jun. 24, 2003)) now U.S. Pat. No. 7,468,261; Ser. No. 10/607,136 (filed Jun. 27, 2003), now U.S. Pat. No. 7,226,738; Ser. No. 10/686,713 (filed Oct. 17, 2003) U.S. Pat. Pub. No. 2004-0175724; Ser. No. 10/976,240

(filed Oct. 29, 2004-) U.S. Pat. Pub. No. 2005-0214796; Ser. No. 10/790,766 (filed Mar. 3, 2004) now U.S. Pat. No. 7,473,775; Ser. No. 10/488,971 (filed Oct. 18, 2004) now U.S. Pat. No. 7,470,511; and Ser. No. 10/551,775 (filed Sep. 14, 2006) U.S. Pat. Pub. No. 2006-0204964 the contents of each of which are incorporated by reference herein in their entirety.

Example 2

Mass Spectrometry Detection of Abscripts

Figure 4:
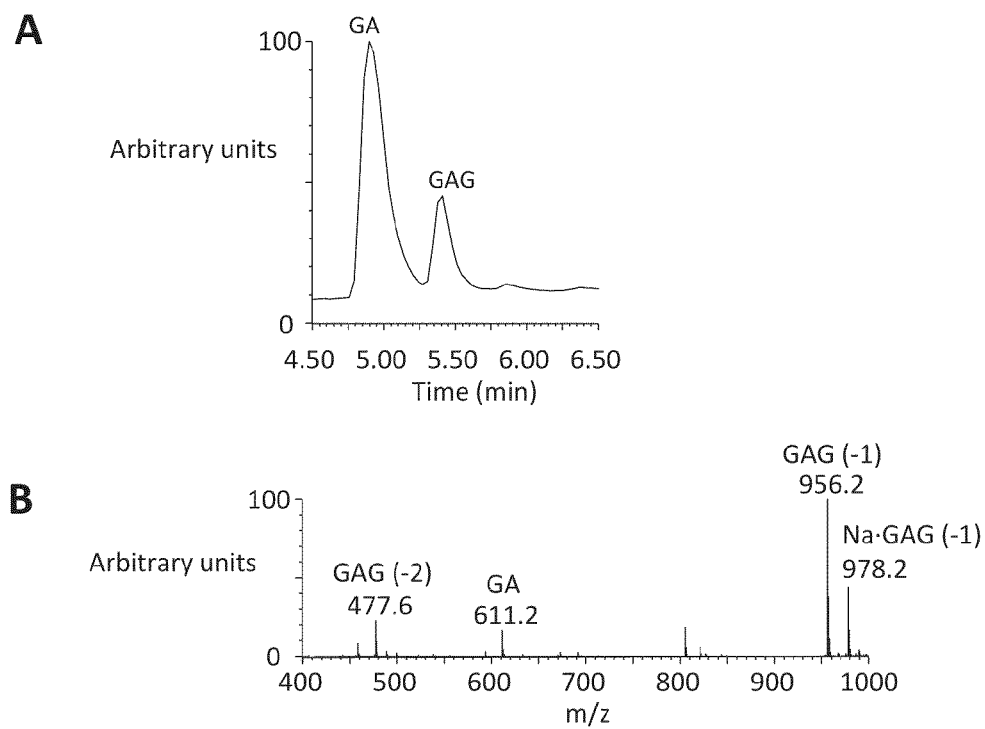
FIGS. 4A and 4B illustrate detection of Abscripts by mass spectrometry. An Abscription® reaction that included the initiator GpA and GTP was fractionated by reverse-phase HPLC. The output of the column was introduced into a mass spectrometer.

Trinucleotide Abscripts are detected by mass spectrometry following their fractionation from dinucleotide initiators by HPLC. The output of the fractionation is plotted as total ion count verses chromatographic retention time as illustrated in FIG. 4A. The chromatographic profile for any ion can be similarly plotted. The contributions of particular m/z species at a specific retention time can be summed to give the amount of Abscript as the area under the chromatographic peak. FIG. 4B shows the ion spectrum associated with the Abscript GAG (retention time of 5.4 min). The yield of GAG would be the sum of species with m/z values of 477.6, 956.1 and 978.2. These species account for doubly charged, singly charged and the sodium adduct respectively.

Example 3

Preparation of GST-MBD Protein

Figure 5:
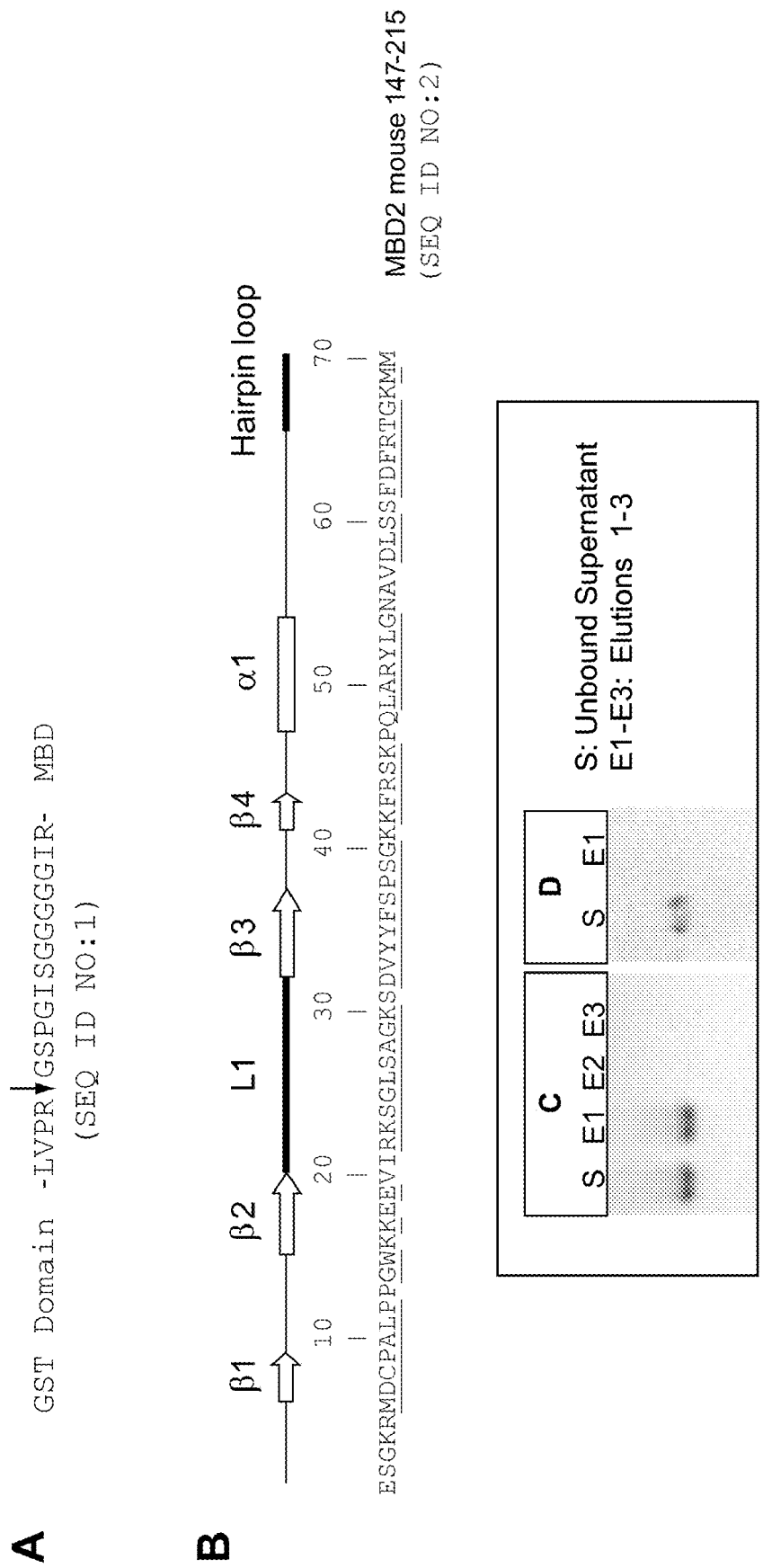
FIG. 5 is an illustration of the structure of a GST-MBD Protein used in methylation detection methods of the invention.

A GST fusion protein that contains the methyl binding domain (MBD) from mouse MBD2 was constructed as illustrated in FIG. 5. The codons for the MBD domain were optimized for expression in *E. coli*. The construct contains a thrombin cleavage site between the GST and MBD domains. The GST protein also contains four surface cysteine residues that were used for attachment of APCs or Biotin. The details of the GST-MBD protein are provided in U.S. Patent Application No. 61/053,648, filed May 15, 2008 (now U.S. Patent Publication No. 2009-0298080) the contents of which are incorporated by reference herein, and in particular, Examples 2-11 describing the preparation and use of MBD fusion proteins.

The GST domain allows the fusion protein, or its complexes with methylated DNA, to be isolated on Glutathione resins or beads and eluted with glutathione, or to be captured or detected with antibodies that recognize GST.

MBD from the MBD2b protein was chosen for final constructs because MBD2b has the highest affinity among the known methyl CpG binding proteins for Me-CpG sites and the lowest cross reactivity with unmethylated CpGs. It has between a 25 to 100 fold higher affinity for Me-CpG sites than does MeCP2, and a 9.7 to 43 fold higher preference for methylated DNA than does MeCP2 (Fraga et al. (2003) Nucleic Acids Res., 31:1765-74). Additionally, there are no sequence context effects on MBD2 CpG recognition, as there are for MeCP2, which requires a run of 4 A-Ts near a CpG site. Therefore a greater number of mCpG sites are recognized by MDB2 than by MeCP2.

Example 4

Immobilized GST-MBD2 Retains High Specificity for Methylated DNA Even with 2 ng or Less of Input DNA The GST-MBD protein was attached to glutathione magnetic beads and used to isolate varying amounts of methylated DNA to determine the minimum starting DNA sample size that could be recovered with high specificity. HeLa genomic DNA or HeLa DNA artificially methylated with SssI methylase was incubated with GST-MBD magnetic beads for 1 hour at 22° C. with horizontal rotary mixing at 1000 rpm. Bound DNA was eluted from the beads after removal of the supernatant containing unbound DNA, by incubation at 80° C. for 10 min with horizontal rotary mixing at 1000 rpm. Eluted DNA samples were tested for the presence of PTGS2 (GenBank GI:34576917) DNA by qPCR using the primer pair 5'-ggtacgaaaaggcggaaaga-3' (SEQ ID NO:6) and 5'-tgtgg-gaaagctggaatatc-3' (SEQ ID NO:7) with SYBR® Green dye for detection. PTGS2 is unmethylated in HeLa and was expected to remain in the supernatant of the binding reaction. A recovery of 94% of a 2 ng genomic DNA input of artificially methylated DNA was observed in the eluted fraction while 100% of the unmodified PTGS2 DNA from HeLa was recovered in the supernatant fraction as expected. At an input of 1 ng of methylated HeLa DNA, 73% of PTGS2 DNA was bound and recovered with heat elution. No binding of the unmethylated version from unmodified HeLa was detected. The lowest DNA amount (2 ng) which could be visualized by agarose gel electrophoresis staining corresponds to approximately 300 cells. Even less DNA can be isolated and detected using Abscription® for amplicon detection.

Example 5

Abscription® Based CpG Methylation Assay

FIG. 6 illustrates an overall protocol for determining the methylation status of multiple CpG islands. Briefly, fragmented methylated DNA from a genomic DNA sample is isolated, followed by amplification of specific CpG islands whose methylation status is under investigation. For the amplification, one primer contains an affinity tag, such as biotin, which allows retrieval and immobilization of the island. The second primer contains a sequence for attachment of the Abortive Promoter Cassette.

This method permits the amplification and isolation of as many CpG islands in a sample as compatible PCR primers can be designed. Because the DNA is not deaminated with bisulfite treatment, which results in the conversion of "C"s to "dU", the problematic issues for high level multiplexing associated with the loss of sequence heterogeneity caused by deamination, are avoided. Since the primer sites are not rigidly limited to specific sequences in the target, there is sufficient flexibility in primer placement to allow the design of multiple compatible primer sets (Henegariu et al. Biotechniques (1997) 23:504-11; Onishi et al. J. Agric. Food Chem. (2005) 53:9713). A different APC is attached to each target CpG island, thereby generating a different Abscript signal for each. Thus, simultaneous detection of multiple CpG islands from a single sample can be achieved.

Briefly, native genomic DNA is fragmented and then bound to glutathione beads containing the Glutathione-S-Transferase (GST)-Methyl Binding Domain (MBD) fusion protein described above in EXAMPLE 3. Only methylated DNA binds (FIG. 6A, Step 1). After washing, the methylated DNA is eluted from the beads (FIG. 6A, Step 2) and islands to be interrogated are amplified by PCR (FIG. 6B. Step 3). One of the primers contains a capture tag (e.g. biotin) at the 5' end (FIG. 7A). The second primer contains 2 regions. The first is a polynucleotide sequence complementary to the target DNA. The second region is an arbitrary sequence dissimilar to the target DNA or other islands (FIG. 7A). This second sequence is complementary to a Target Attachment Probe (TAP)

sequence which is linked to an Abortive Promoter Cassette (APC). The complement to the TAP sequence is called an anti-TAP sequence (α-TAP). The α-TAP sequence remains single-stranded during the PCR amplification of the target DNA due to the inclusion of a non-natural nucleotide at the junction between the primer sequence that hybridizes to the target and the α-TAP sequence (the EA nucleotide in FIG. 7A). After amplification, the islands are immobilized, for example on streptavidin beads (FIG. 6B, Step 4), and remaining genomic DNA and primers are washed away. The TAP-APC polynucleotide is then contacted with the amplified target DNA and hybridizes to the single-stranded anti-TAP sequence (FIG. 6C, Step 5). Free TAP-APC is washed away, and Abscription® reagents are added to generate Abscript signals (FIG. 6C, Step 5). Further details of the method are given below.

Step 1: Cutting of Genomic DNA

The initial digestion step was designed to generate fragments that contain CpG islands or large portions thereof. The restriction sites were chosen to fall outside of the region to be analyzed and are neither methylation dependent nor methylation sensitive. Restriction enzymes with 4 base recognition sequences were used. Table 1 lists the fragment sizes generated by MseI or DdeI for a sample of 6 CpG islands reported to be differentially methylated. Up to 3 μg of genomic DNA routinely were digested with 20 units of MseI (NEB, Beverly, Mass.) in the vendor's restriction buffer (NEB buffer 4). Cleavage reactions were incubated for at least 8 hr at 37° C. The extent of cleavage was measured by performing PCR on a sample of the digest using a primer that contains the MseI sequence. Positive controls are genomic DNA untreated with MseI and an amplification reaction of the MseI treated DNA using primers that are unaffected by MseI digestion.

The purpose of the digestion is to unlink the target islands from neighboring CpG sequences that might be normally methylated and thereby cause the transfer of an unmethylated island to the methylated DNA fraction. In most cases either MseI or Dde I produced a single fragment that accounts for the bulk of the island sequence without including many neighboring sequences. The exception was the excessive cleavage of MGMT with DdeI. In this case, the alternative enzyme produced satisfactory results. In cases where a CpG island is fragmented into several fragments, each segment can be analyzed with its own set of primers.

TABLE 1

CpG Island Cleavage patterns

| CpG Island | Restriction Enzyme | Recognition Sequence | Fragment(s) generated (nt) |
|---|---|---|---|
| APC (GI: 224589817) | MseI DdeI | TTAA CTNAG | 520, 164 820 |
| CCNA1 (GI: 224589804) | MseI DdeI | TTAA CTNAG | 1168 523, 231, 177 |
| GSTP1 (GI: 34576917) | MseI DdeI | TTAA CTNAG | 1936 261, 131 |
| MGMT (GI: 34556) | MseI DdeI | TTAA CTNAG | 1967 Excessively fragmented |
| RARB (GI: 35881) | MseI DdeI | TTAA CTNAG | 612, 163 625 |

TABLE 1-continued

CpG Island Cleavage patterns

| CpG Island | Restriction Enzyme | Recognition Sequence | Fragment(s) generated (nt) |
|---|---|---|---|
| PTGS2 (GI: 211904109) | MseI DdeI | TTAA CTNAG | 516, 417 464, 229, 87, 37 |

Step 2: Isolation and Recovery of Methylated DNA

The methylated DNA capture step was formatted for magnetic beads bearing glutathione. The GST-MBD protein was preloaded onto the beads suspended in the DNA sample after removing excess GST-MBD protein. DNA binding was performed for 1 hr at room temperature (22-24° C.) with mixing to maintain the beads in a suspended state (Eppendorf Thermomixer, 1000 rpm). DNA samples typically contained between 1 ng to 50 ng of genomic DNA in a 50 μl volume of binding buffer. At the completion of the binding step the beads were pelleted to the side of the tube with a rare-earth magnet and the supernatant containing unmethylated DNA was removed. The beads were washed twice with, 400 μl of a wash buffer containing the same NaCl concentration as the binding buffer (160 mM). Each wash was incubated for 5 min at room temperature with mixing (1000 rpm). A final wash was performed with TE buffer (10 mM Tris pH 8, 1 mM EDTA). The beads were suspended in 400 μl TE and immediately pelleted with the magnet. The TE wash buffer was discarded and the beads were suspended in 50 μl of elution buffer (10 mM Tris pH 8, 1 mM EDTA).

Methylated DNA can be eluted from the beads with several alternative methods. Beads in TE buffer can be incubated for 10 min at 80° C. with mixing (1000 rpm). The beads are pelleted with the magnet and the eluted DNA is recovered. In an alternative method the beads are suspended in elution buffer containing 0.1% SDS. Complete elution of bound methylated DNA was achieved with a single 20 min incubation at 50° C. The eluted DNA is ready for PCR without further processing provided a nonionic detergent such as Tween-20 is included in the PCR buffer (see Goldenberger et al. PCR Methods Appl. (1995) 4:368-70). Elution can also be performed with exposure of the beads for 10 min to elution buffer containing a minimum of 20 mM reduced glutathione at pH 8. FIG. 5C shows the results of the fractionation of the SNRPN CpG island of HeLa DNA. Methylated DNA was released with heat treatment. SNRPN is an imprinted gene. One copy is fully methylated and the other copy is normally unmethylated. As expected half of the SNRPN copies were found in the supernatant (FIG. 5C fraction S, unmethylated fraction) and half of the copies were eluted from the beads in the first elution (FIG. 5C, fraction E1, methylated fraction). All of the methylated DNA was extracted in the first elution. Two serial elutions after the first elution (E2 and E3) did not contain SNRPN DNA. The CpG island of the PTGS2 gene (unmethylated in HeLa) was used as a negative control (FIG. 5D). All of the PTGS2 DNA appeared in the supernatant fraction.

Step 3: PCR Amplification with Tagged Primers

CpG island segments were amplified and labeled with a biotin affinity tag and a single-stranded oligonucleotide sequence that is used for attachment of an abortive promoter cassette (APC). PCR reactions contained 1× Hot Start Taq buffer (Fermentas) 0.8 mM dNTPs (0.2 mM each), 2 mM $MgCl_2$, and 5% (v/v) DMSO. The biotinylated primer and the α-TAP primer were present at 1 μM each. Amplifications were performed with 2 units/20 μl reaction of TrueStart™ hot start Taq DNA polymerase (Fermentas). One unit equals the incorporation of 10 nmol of dNTPs in 30 min at 74° C. The cycling conditions were 95° C. for 1 min, followed by up to 32 cycles of 95° C. for 30 sec, 62° C. for 30 sec, and 72° C. for 30 sec. A final elongation step was at 72° C. for 5 min. Completed reactions were held at 4° C. FIGS. 5C and 5D show detection of the fractionated, amplified DNAs by agarose gel electrophoresis.

α-TAP Primer Sequence Design

Primers were optimized for high signal intensity by minimizing interactions among the three oligonucleotide primer/α-TAP sequences that are present in the PCR reaction. The biotinylated PCR primer and the 3' end of the α-TAP were used to prime DNA synthesis during the amplification and were designed using primer software (Oligo Explorer 1.2) to minimize primer:primer interactions and the formation of primer hairpin loops. The α-TAP at the 5' end of the second primer was designed to be incorporated into the amplicon and remain single-stranded due to the presence of a non-coding nucleotide, ethenoA (εA), which separates the primer sequence from the α-TAP. Most DNA polymerases including Taq polymerase cannot incorporate a dNTP opposite εA and terminate synthesis (FIG. 7) (see Patel et al. J. Biol. Chem. (2001) 276:5044-51). The nucleotide analog prevents the α-TAP sequence from being copied during PCR. Potential interactions between the α-TAP sequence and either primer sequence are minimized to avoid inhibition of PCR and false positive results from nonspecific immobilization of a fully single-stranded α-TAP.

Primer design went through 3 steps. First the priming sequences were optimized within the following criteria: 1) a primer length between 16 to 20 nt; 2) a $T_m$ close to 60° C.; 3) primer-primer interactions with base paired 3' ends were eliminated; 4) other primer-primer interactions must have a $T_m$ of <16° C.; and 5) hairpin structures with $T_m$>8° C. were rejected. Primer pairs for 6 CpG islands were successfully developed using these criteria.

The second step in primer optimization was to eliminate hairpin structures in the α-TAP-primer oligonucleotide that might interfere with PCR or attachment of a TAP-APC. A collection of 6 α-TAP candidate sequences were designed based on RNA phage MS2, fr and Qβ sequences. Each candidate α-TAP was tested in silico and those that formed hairpins with a $T_m$>26° C. under our TAP-annealing conditions were modified to eliminate the hairpin and retested (Zuker, Nucleic Acids Res. (2003) 31:3406-15). The only limitation in modifying α-TAP sequences was that they do not acquire significant complementarity with the priming sequences. Potential hairpin interactions between an α-TAP and a linked primer sequence were tested in silico and if necessary the α-TAP sequence was changed to minimize hairpin stability and/or prevent primer extension from a hairpin. An exemplary primer-α-TAP oligonucleotide (SEQ ID NO:42) has a hairpin structure with a $T_m$ of 41° C. under PCR conditions used, but amplified CDKN2A DNA as efficiently as the primer lacking the α-TAP extension in combination with reverse primer SEQ ID NO:43. Finally, interactions between the α-TAP and the biotinylated primer were tested in primer design software using a CpG island sequence file with the α-TAP appended at the end of the file and choosing it as a primer along with the biotinylated primer sequence. α-TAP and reverse primer pairs were developed for CpG islands associated with the α-TAP appended at the end of the file and choosing it as a primer along with the biotinylated primer sequence. α-TAP and reverse primer pairs were developed for CpG islands as listed below in Table 2.

TABLE 2

α-TAP and Reverse Primer Pairs

| CpG Island | α-TAP primer | Reverse Primer |
|---|---|---|
| DAPK1 (SEQ ID NO: 44) | 5'-cacaggtcaaaggtc ataaaaatg[εA]TTtccc ataccaagcaccgt-3' (SEQ ID NO: 8) | 5'-Biotin-gtcctcctc acactccg-3' (SEQ ID NO: 9) |
| GAPDH (SEQ ID NO: 45) | 5'-caccgtcgaatc tctcc[εA]ccg tgtgcccaagacc-3' (SEQ ID NO: 10) | 5'-Biotin-gtgcctttc attccatccagcc-3' (SEQ ID NO: 11) |
| GSTP1 (SEQ ID NO: 47) | 5'-ccaagaagcca cacgaca[εA]gcgg gaccctccagaa-3' (SEQ ID NO: 12) | 5'-Biotin-actcactg gtggcgaagact-3' (SEQ NO ID: 13) |
| MGMT (SEQ ID NO: 46) | 5'-cctccatcccaa agtA[εA]cctctg ctccctccgaa-3' (SEQ ID NO: 14) | 5'-Biotin-ccgatggcct agacactg-3' (SEQ ID NO: 15) |
| PTGS2 (SEQ ID NO: 48) | 5'-gaaaggactacaa aggacaga[εA]ggtac gaaaaggcggaaaga-3' (SEQ ID NO: 16) | 5'-Biotin-tgtgggaaa gctggaatatc-3' (SEQ ID NO: 17) |
| SNRPN (SEQ ID NO: 49) | 5'-cgaaaatgcatc tgagtagc[εA]accctcg cctaaaatccctatg-3" (SEQ ID NO: 18) | 5'-Biotin-ggtatcct gtccgctcgca-3' (SEQ ID NO: 19). |

TAP-APC Design.

TAP-APCs were made by hybridizing TAP-APC non-template strands to complementary APC template strands. The APC portions were double-stranded and the TAP segments were a single strands extending from the non-template strands. TAP-APCs were designed so that a collection of APCs either encoded the same abscript for use in single-plex reactions, or a collection of TAP-APCs each encoded a different abscript allowing for multiplex detection. Single-stranded single-plex TAP-APCs were designed for the α-TAPs as indicated below in Table 3.

TABLE 3

Single-Plex TAP APCs

| CpG Island | TAP APC |
|---|---|
| DAPK1 (SEQ ID NO: 44) | 5'-cattttatgacctttgacctgtggctgtt gacacagaataaacgctcaatagtacaatggg tggagaggtgctttagta gtgtt-3' (SEQ ID NO: 26) |
| GAPDH (SEQ ID NO: 45) | 5'-ggagagattcgacggtgctgttgacac agaataaacgctcaatgtacagaga tgggatggagtgctttagtagtgtt-3' (SEQ ID NO: 27) |
| GSTP1 (SEQ ID NO: 47) | 5'-gtcgtgtggcttcttgggctgttgacac agaataaacgctcaatgtacaaatggg atggagaggtgctttagtagtgtt-3' (SEQ ID NO: 28) |
| MGMT (SEQ ID NO: 46) | 5'-tactttgggatggagggctgttgac acagaataaacgctcaatgtacaat gggatggagaggtgctttagtagtgtt-3' (SEQ ID NO: 29) |

TABLE 3-continued

Single-Plex TAP APCs

| CpG Island | TAP APC |
|---|---|
| PTGS2<br>(SEQ ID NO: 48) | 5'-ctgtcctttgtagtcctttcggctg<br>ttgacacagaataaacgctcaatgtac<br>aatgggatggagaggtgctttagtagtgtt-3'<br>(SEQ ID NO: 30) |
| SNRPN<br>(SEQ ID NO: 49) | 5'-gctactcagatgcattttcggctgtt<br>gacacagaataaacgctcaatgtacaatg<br>ggatggagaggtgctttagtagtgtt-3'<br>(SEQ ID NO: 31) |

The single-stranded single-plex TAP-APCs were annealed to a common template strand encoding the same abscript (SEQ ID NO:32).

Multiplex-compatible TAP-APCs were each paired with their own template strand encoding a unique abscript. A collection of multiplex TAP-APCs (Table 4) could be used together to detect the CpG islands listed in Table 4.

TABLE 4

Multiplex-Compatible TSP-APCs

| CpG Island | TAP APC |
|---|---|
| DAPK1<br>(SEQ ID NO: 44) | 5'-catttttatgacctttgacctgtgaaat<br>ttatgtttgacagatcttacaatcgcatgc<br>tataatacactaacggtgctttaaaattccg-3'<br>(SEQ ID NO: 20)<br>5'-cggaattttaaagcaccgttagtggt<br>attatagcatgcattgtaagatctgat<br>caaacataattt-3'<br>(SEQ ID NO: 21) |
| GSTP1<br>(SEQ ID NO: 47) | 5'-gtcgtgtggcttcttggaaatttatgt<br>ttgacagatcttacaatgcatgctgata<br>ataccactaaggtgatataaaattccg-3'<br>(SEQ ID NO: 22)<br>5'-cggaattttatatcaccuucagtgg<br>tattatagcatgcattgtaagatct<br>gtcaaacataaattt-3'<br>(SEQ ID NO: 23) |
| MGMT<br>(SEQ ID NO: 46) | 5'-tactttgggatggagggctgct<br>ggaggcgggtataaatttag<br>ccagcacggccgaatagttatcg-3'<br>(SEQ ID NO: 24)<br>5'-cgaccgtaactattcggtgcttagggc<br>agcgccccgcctccacgagc-3'<br>(SEQ ID NO: 25) |

Step 4 and 5. Attachment of Amplicons to Streptavidin Beads and Binding of TAP-APCs Biotinylated amplicons were bound to streptavidin beads to remove free probes and unbound APCs in succeeding steps of the assay.

In optimization experiments, complete binding of amplicons to the streptavidin magnetic beads in the presence of 10 pmol of biotinylated primer was observed with a total binding capacity of 40 pmol of biotinylated oligonucleotide. The binding time was optimized to minimize the time course of the assay using agarose gel electrophoresis to measure the removal of the amplicons from the buffer phase of the binding reaction. Quantitative binding of the biotinylated amplicons was observed within 5 min. of mixing the beads and the DNA samples.

Attachment of the TAP-APC to the amplicon was successfully performed either free in solution before the addition of streptavidin beads or after binding the amplicons to the beads followed by a wash step to remove free primer-αTAP oligonucleotides. The $T_m$s for the TAPs range between 55.8-64° C. under the annealing conditions used (150 mM Na$^+$). TAP-APC was added at 0.5 μM and incubated at 51° C. for a minimum of 15 min. High stringency was not required to achieve efficient binding. Analysis of the TAPs and α-TAP s indicated that hairpin formation was insignificant under these annealing conditions. The sequence complexity of the reaction was low even in preparations subjected to multiplex PCR. At most 3 pairs of α-TAPs and TAPs are present in a triplex reaction and these sequences can be arbitrarily changed to prevent cross-hybridization. This annealing step was optimized with respect to temperature in a gradient thermocycler and the shortest annealing time was determined using electrophoretic mobility shift of the amplicon as an endpoint.

The PCR reactions were diluted 1:1 in DNA binding buffer to give a final NaCl concentration of 150 mM. The appropriate TAP-APC was added to each DNA sample to a final concentration of 0.5 μM, followed by an incubation at 51° C. for a minimum of 15 min.

Streptavidin magnetic beads were aliquoted to PCR tubes. The beads were washed with 100 μl of 50% (v/v) binding buffer. The washed beads were suspended in the DNA samples followed by incubation at 51° C. for a minimum of 5 min.

The binding reaction was terminated by pelleting the beads with a magnet and removing the binding buffer. The beads were subjected to 2 washes in 180 μl of wash buffer containing the same NaCl concentration as the 50% (v/v) binding buffer (150 mM). Each wash step included a 5 min incubation at 51° C. to replicate the stringency of the binding reaction and then the beads were rapidly pelleted with the magnet. A third wash was in 40 mM HEPES pH 7.5, 40 mM KCl. The beads could be stored refrigerated or could be immediately subjected to Abscription®.

Step 6: Abscription®

Beads containing bound amplicon:TAP-APCs were pelleted with a magnet to remove storage buffer and were suspended in 10 μl of Abscription® buffer containing 1 mM dinucleotide initiator (GpA), 1 mM NTP (GTP) and 0.4 units of RNA polymerase. One unit catalyzes the incorporation of 1 nmol of NTP in 60 min at 65° C. Abscription® reactions were incubated for 1 hr at 77° C.

Abscripts were detected by UV-shadowing by spotting 1.5 μl samples onto a silica gel TLC plate containing a fluor. TLCs were developed in an air-tight chamber containing 100 ml of solvent (Isopropanol:Ammonium hydroxide:Activator solution, 6:3:1). Abscripts were detected as dark spots under shortwave UV light as illustrated in FIG. 8B (UV-shadowing).

For LC-MS detection, 10 µl of Abscription® reaction was diluted into 20 µl of HPLC grade water in a 384 well plate. Ten microliters was processed and quantified by LC-MS as illustrated in FIG. 8C.

TABLE 5

Sensitivities of TaqMan ® and Abscription ® assays

| TaqMan ® | | Abscription ® (1.5 hr) | | | |
|---|---|---|---|---|---|
| | | TLC | | LC-MS | |
| Copies | C$_t$ | Cycles | LOD (copies) | Cycles | LOD (Copies) |
| 9000 | 28 | 29 | 100 | 29 | 30 |
| 3000 | 30 | | | | |
| 1000 | 32 | | | | |
| 300 | 34 | | | | |
| 100 | 35 | | | | |
| 30 | 37 | | | | |

Figure 8:
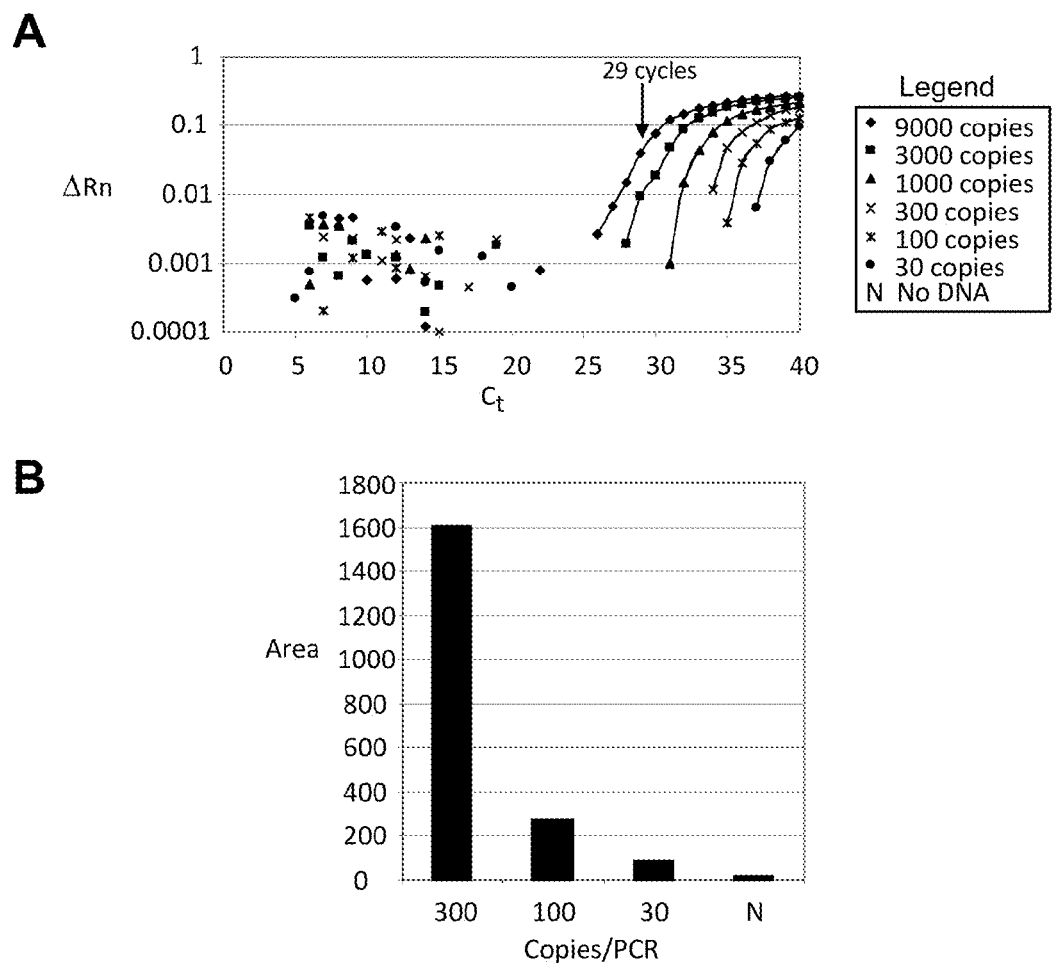
FIG. 8. shows the relative sensitivities of DNA detection by TaqMan® PCR versus the Abscription®/PCR method depicted in FIG. 6. A fragment of the GSTP1 CpG island from unfractionated methylated HeLa DNA was amplified from starting copy numbers/PCR of 9000 to 30.

FIG. 8 shows the results of α-TAP Abscription®-based detection of titrated HeLa compared to Taq®Man PCR using the same priming sites for both methods. 5'-gcgggaccctccagaa-3' (SEQ ID NO:3) and 5'-actcactggtggcgaagact-3' (SEQ ID NO:4) were used for the qPCR amplification. 5'-FAM-accacccttataaggctcggaggcc-Iowa Black™ FQ quencher-3' (SEQ ID NO:5) was the fluorescent probe. 5'-actcactggt ggcgaagact-3' (SEQ ID NO: 13) and 5'-cctccatcccaaagta[εA]gcgggaccctccagaa-3' (SEQ ID NO: 12) were the α-TAP primer pair. FIG. 8B shows the results for TLC detection. Abscription/PCR primers were SEQ ID NO:12 and SEQ ID NO:13. The TAP-APC was made by annealing SEQ ID NO:28 and SEQ ID NO:32. The APC encoded the Abscript GAG. Abscripts were detected using thin layer chromatography (TLC) and UV shadowing. The limit of detection (LOD) at 29 cycles using UV-shadowing was 100 copies. FIG. 8C shows the LC-MS detection results for the same samples analyzed in FIG. 8B. DNA inputs for the PCR reactions varied from 30 to 9000 genomic copies. The LOD for LC-MS at 29 cycles was 30 copies. Area refers to the area of the chromatographic peak containing the Abscript (GAG).

TaqMan® PCR required 35 cycles for detection of 100 copies and 37 cycles for detection of 30 copies (FIG. 8A and Table 5). Abscription® based detection was more sensitive than TaqMan® even with TLC and UV-shadowing.

Figure 9:
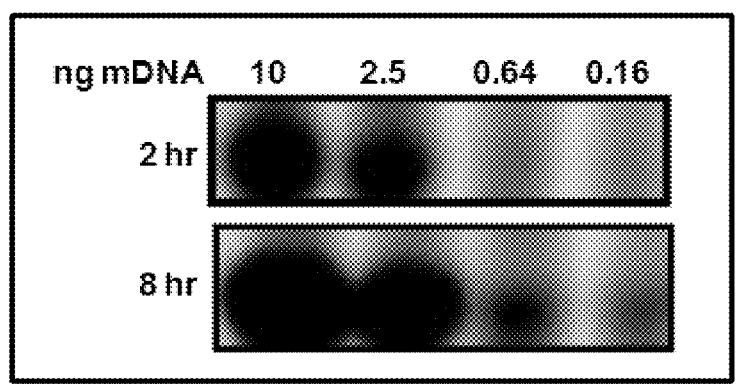
FIG. 9 shows detection of CY5™ labeled Abscripts using TLC after PCR amplification of the indicated amounts of input DNA followed by 2 hr and 8 hr of Abscription®.

TLC based detection is more sensitive if UV-shadowing is replaced with detection of fluorescent Abscripts. Genomic DNA that was methylated in the CDKN2A CpG island was amplified with primers containing a biotin group (SEQ ID NO:43) and an anti-TAP sequence (SEQ ID NO:42). Amounts of starting genomic DNA were 10 ng, 2.5 ng, 640 pg, and 160 pg. This corresponded to 3000, 750, 188 or 47 copies of genomic DNA. After addition of the TAP-APC encoding AUC, Abscription® was carried out in the presence of the Cy5™ labeled dinucleotide ApU and CTP at 45C. Samples were withdrawn (1 µl) and analyzed by rapid TLC. Abscripts from 2.5 ng of starting DNA could be visualized after 2 hr of Abscription®, and 47 copies could be detected easily after 8 hours of Abscription® as shown in FIG. 9.

In this experiment, the Abscription® product was the Cy5™-labeled trinucleotide AUC. Cy5™ is actually a rather poor initiator compared to several other fluorescent dyes, reducing the turnover for trinucleotide synthesis to about 8% of that with unlabeled dinucleotides. For this reason, Cy5™ may not be the dye of choice for these assays, but can be replaced with other dyes, such as fluorescein or DyLight (Pierce), both of which give turnovers closer to 35% of that obtained with unlabeled initiators. By using dyes with approximately 4 fold higher efficiency, times may be reduced correspondingly, allowing detection of less than 50 copies of starting DNA in 2 hours. Fluorescein has the additional advantage of being detectable with a low cost, long wavelength UV light.

Example 6

Two-Step CpG Island Methylation Detection with APC-Primers

Using a two step detection method, methylated DNAs were isolated from a fragmented genomic DNA sample as in the three-step α-TAP method (EXAMPLE 5). Methylated DNA fragments were bound to immobilized GST-MBD protein (FIG. 10; Step 1) as described above. Methylated fragments were released by exposure to heat or glutathione after washes to remove unmethylated DNA (FIG. 10; Step 2).

Targeted CpG islands were amplified and tagged using a primer that contains an APC sequence at its 5' end (FIG. 10; Step 3). The single-stranded form of the APC is inactive but becomes activated when it is converted into a double-stranded form during amplification of the target (FIG. 10; Step 4). Thus, Abscription® can be performed during the PCR reaction if initiator(s) NTP(s) and RNAP are included (FIG. 10; Step 6).

Example 7

Design and Validation of APC-Primers

APC-primers were designed to avoid self priming and the formation of primer dimers with the reverse primer. At least some of these events are likely to produce active duplex promoters that could would create high levels of background Abscription®. Potential primer sequences were screened as described in EXAMPLE 5 for the potential to form primer dimers and to self prime. The APC portion of the APC primer is 44 nt long of this 33 nt can be changed without significantly affecting Abscription® activity. In most cases potential self priming or primer dimer interactions could be eliminated by changing the sequence of the APC segment of the APC-primer.

Primer pairs that were predicted to be free of potential interactions were tested by performing PCR reactions in the absence of DNA over a range of annealing temperatures to determine if the primers alone could produce background signal. First the APC-primer was tested to determine the level of self priming. Next, PCR reactions without DNA were performed with both the APC primer and the reverse primer to test for primer dimer effects. Completed PCR reactions were supplemented with 1 mM dinucleotide intiator, 1 mM NTP, 0.4 units of RNA polymerase and were analyzed by Abscription®. FIG. 11 shows the Abscription® results for a well designed primer pair (SEQ ID NO:33 and SEQ ID NO:34) that targets the GAPDH CpG island. FIG. 11A shows the TLC data for the APC primer alone (SEQ ID NO:34) and for the primer pair along with a positive control that included HeLa genomic DNA. The encoded Abscript GAG could only be detected in the positive control. FIG. 11B shows LC-MS data for the same samples. Only the positive control produced the Abscript, while the reactions lacking DNA did not produce significant signal over a broad range of annealing temperatures. APC-primer/reverse primer pairs developed for CpG islands are given in Table 6 below.

TABLE 6

APC-Primer/Reverse Primer Pairs

| CpG Island | APC Primer | Reverse Primer |
|---|---|---|
| GAPDH (SEQ ID NO: 45) | 5'-agagaattttttcataaac attaaatgtacaatgggaacg agaaccgtgtgcccaagacc-3' SEQ ID NO: 33 | 5'-ctgcctagg gagagaga-3' SEQ ID NO: 34) |
| MGMT (SEQ ID NO: 46) | 5'-gctgttgacaattaat aaacgctcaatgtacaatgggactga gactcttaggcttctggtggc-3' (SEQ ID NO: 35) | 5'-cctgtggt gggcgatgc-3' (SEQ ID NO: 36) |
| PTGS2 (SEQ ID NO: 48) | 5'-tgcgaaccttgactataaaaat tcaatgtacaatgggacggagaa ggtacgaaaaggcggaaaga-3' (SEQ ID NO: 37) | 5'-tgtgggaaag ctggaatatc-3' (SEQ ID NO: 38) |
| SNRPN (SEQ ID NO: 50) | 5'-gctgttgacacagttcaa acgctcaatgtaaaatgggacaat cacctccgcctaaaatccctatg-3' (SEQ ID NO: 39) | 5'-cttgctgtt gtgccgttctg-3' (SEQ ID NO: 40) |

TABLE 6-continued

APC-Primer/Reverse Primer Pairs

| CpG Island | APC Primer | Reverse Primer |
|---|---|---|
| GSTP1 (SEQ ID NO: 47) | 5'-gctgaagacacagaataa acgatcaatgtataatgggactgag agcgggaccctccagaa-3' (SEQ ID NO: 41) | 5'-actcactggt ggcgaagact-3' (SEQ ID NO: 4) |

Example 8

Comparison of Detection of Methylated DNA from Tumor Cell Lines with α-TAP and APC-Primer Methods PCR reactions were performed with 0.4 units of Hot Start Taq (Fermentas) in the vendor's 1× buffer containing 2 mM MgCl2, 0.8 mM dNTPs (0.2 mM each), and 5% (v/v) DMSO. One unit of Hot Start Taq incorporates 10 nmol of dNTPs in 30 min at 74° C. The APC-primer and the reverse primer were at 1 µM each. The cycling conditions were 95° C. for 1 min, followed by up to 32 cycles of 95° C. for 30 sec, 62° C. for 30 sec, and 72° C. for 30 sec. A final elongation step was at 72° C. for 5 min. Completed reactions were held at 4° C. Completed PCR reactions (10 µl) were supplemented with 1 mM dinucleotide initiator, 1 mM NTP and 0.4 units of RNA polymerase. Abscription® was then performed for up to 1 hr at 77° C.

Abscription® could be performed during PCR if the dinucleotide initiator and the NTP were included in the PCR reaction at 1 mM each. A thermostable RNA polymerase was added at 0.4 units per 20 µl reaction. One unit catalyzes the incorporation of 1 nmol of NTP in 60 min at 65° C. Abscription® reactions were incubated for 1 hr at 77° C. Abscripts could be detected as described in examples 2 and 5.

TABLE 7

Percent Methylation of Tumor Cell DNAs

| DNA sample Detection method | Percent methylation ± SD | | | | | |
|---|---|---|---|---|---|---|
| | DAPK1 | MGMT | GSTP1 | PTGS2 | GAPDH | SNRPN |
| LNCaP (Prostate) α-TAP detection | 81 n = 2 | 19 n = 2 | 100 n = 2 | 60 | 0.8 ± 0.3 n = 3 | 49 ± 1.5 n = 3 |
| LNCaP APC-primer detection | | | 99 ± 1.1 n = 4 | | 3.3 ± 3.6 n = 3 | 49 ± 2.9 n = 3 |
| MDA-PCA-2b (Prostate) α-TAP detection | | | | 66 | 0 | |
| HeLa (Cervical) APC-primer | | 96.5 ± 3.0 n = 5 | | 0 n = 2 | 4.8 | 48 ± 2.9 n = 7 |

Table 7 shows the results of Abscription®-based detection of methylated DNA from tumor cell lines. Most replicate measurements were done with samples measured once from multiple fractionation experiments. The GAPDH CpG island was unmethylated which was expected if the tumors maintained the normal methylation status in this island. The SNRPN CpG island fit the prediction for an imprinted gene. The other islands were consistent with published results except for DAPK1 in LNCaP for which there are divergent conclusions on its methylation status (Yegnasubramanian et al. (2004) Cancer Res. 64:1975-86; Lin et al. (2001) Am J. Pathol. 159:1815-26; Paz et al. (2003) Cancer Res. 63:1114-21; Toyota et al. (2000) Cancer Res. 60-4044-48; Lodygin et al. (2005) Cancer Res. 65:4218-27).

What is claimed is:

1. A method for detecting at least one target polynucleotide in a sample comprising:
  a) contacting a sample containing the at least one polynucleotide with a primer pair that specifically hybridizes to and amplifies a target sequence of the at least one polynucleotide, wherein the primer pair consists of:
    i) a first primer comprising
      (1) a 3' sequence complementary to a first sequence flanking the target sequence of the polynucleotide, and
      (2) a 5' capture tag;
    and
    ii) a second primer comprising:
      (1) a 3' sequence complementary to a second sequence flanking the target sequence of the polynucleotide, and
      (2) a 5' sequence that provides a means for directing Abscription;
  b) amplifying the target sequence from the first and second primers;
  c) contacting the amplified target sequence with an immobilized molecule that binds the 5' capture tag, thereby capturing the amplified target sequence of the polynucleotide;
  d) transcribing at least one Abscript from the means for directing Abscription;
  and
  e) detecting at least one Abscript transcribed in step d).

2. The method of claim 1, wherein unbound reagents, primers and polynucleotides are washed from immobilized and captured polynucleotides prior to steps c-e.

3. The method of claim 1, wherein amplifying consists of performing a polymerase chain reaction.

4. The method of claim 3, wherein the polymerase chain reaction is performed with at least one of a thermostable DNA polymerase and a thermostable RNA polymerase.

5. The method of claim 1, wherein the 5' capture tag is biotin and the molecule that binds to the 5' capture tag is streptavidin.

6. The method of claim 1, wherein the molecule that binds to the 5' capture tag is immobilized on a solid support selected from a magnetic bead and a microtiter plate.

7. The method of claim 1, wherein a detectably labeled nucleotide is incorporated into the at least one Abscript during step d).

8. The method of claim 7, wherein the detectably labeled nucleotide is a fluorescent nucleotide.

9. The method of claim 1, wherein detecting the at least one Abscript comprises mass spectrometry, capillary electrophoresis or thin layer chromatography.

10. The method of claim 1, wherein the at least one Abscript is 3-20 nucleotides in length.

11. The method of claim 10, wherein the at least one Abscript is 3 nucleotides in length.

12. The method of claim 1, wherein the means for directing Abscription comprises an abortive promoter cassette (APC).

13. The method of claim 1, wherein the means for directing Abscription comprises:
  i) A 5' anti-Target Attachment Probe (α-TAP) sequence that identifies a unique CpG island; and
  ii) a non-natural nucleotide between the 5' α-TAP sequence and the 3' sequence complementary to the second sequence flanking the target sequence;
and step d) comprises:
  i) hybridizing a probe to the amplified target sequence, wherein the probe comprises a 5' Target Attachment Probe (TAP) sequence complementary to the α-TAP sequence and a 3' APC;
and
  ii) transcribing at least one Abscript from the APC.

14. The method of claim 13, wherein the non-natural nucleotide prevents replication of the α-TAP during amplification, and thereby the α-TAP sequence remains single-stranded during steps a) through c).

15. The method of claim 14, wherein the non-natural nucleotide is etheno-deoxyadenosine.

16. The method of claim 1, wherein the at least one target polynucleotide comprises a plurality of different target polynucleotides, and steps a) through e) are carried out simultaneously with a plurality of first and second primer pairs, each primer pair specifically hybridizing to a different target.

17. The method of claim 16, wherein the means for directing Abscription produces a unique Abscript for each of the plurality of targets.

18. The method of claim 17, wherein the unique Abscripts are distinguishable from each other on the basis of molecule weight or nucleotide sequence.

19. The method of claim 16, wherein the plurality of different target comprises at least 10 different targets.

20. The method of claim 1, wherein the at least one target polynucleotide is a methylated CpG island and the sample comprises isolated methylated genomic DNA fragments.

21. The method of claim 20, wherein the methylated genomic DNA fragments are isolated by:
  a) cleaving a genomic DNA sample containing at least one methylated target polynucleotide with a restriction enzyme that does not cleave the target polynucleotide CpG island;
  b) contacting the cleaved genomic DNA with an immobilized Methyl CpG Binding Domain (MBD), thereby immobilizing methylated genomic DNA from the sample; and
  c) optionally, recovering the methylated genomic DNA from the immobilized MBD, thereby isolating methylated genomic DNA fragments.

22. The method of claim 21, wherein the MBD is a GST-MBD2 fusion protein.

23. The method of claim 22, wherein the GST-MBD2 fusion protein is immobilized on a glutathione-containing solid support.

* * * * *